United States Patent
Raab et al.

(10) Patent No.: US 8,224,578 B2
(45) Date of Patent: Jul. 17, 2012

(54) METHOD AND DEVICE FOR OPTIMIZING A NUCLEOTIDE SEQUENCE FOR THE PURPOSE OF EXPRESSION OF A PROTEIN

(75) Inventors: David Raab, Beratshausen (DE); Marcus Graf, Regensburg (DE); Frank Notka, Regensburg (DE); Ralf Wagner, Regensburg (DE)

(73) Assignee: Geneart AG, Regensburg (DE)

( * ) Notice: Subject to any disclaimer, the term of this patent is extended or adjusted under 35 U.S.C. 154(b) by 1168 days.

(21) Appl. No.: 10/539,208

(22) PCT Filed: Dec. 23, 2003

(86) PCT No.: PCT/EP03/14850
§ 371 (c)(1),
(2), (4) Date: May 24, 2006

(87) PCT Pub. No.: WO2004/059556
PCT Pub. Date: Jul. 15, 2004

(65) Prior Publication Data
US 2007/0141557 A1    Jun. 21, 2007

(30) Foreign Application Priority Data
Dec. 23, 2002   (DE) .................. 102 60 805

(51) Int. Cl.
*G01N 33/48* (2006.01)
*C12Q 1/68* (2006.01)
*G06G 7/58* (2006.01)
*G06F 7/60* (2006.01)
*G06F 17/00* (2006.01)

(52) U.S. Cl. .................. 702/19; 435/6; 702/20; 700/90; 703/2; 703/11

(58) Field of Classification Search .................. None
See application file for complete search history.

(56) References Cited

U.S. PATENT DOCUMENTS
2002/0072864 A1   6/2002 Lacroix et al.

FOREIGN PATENT DOCUMENTS
| DE | 199 14 808 A1 | 10/2000 |
| EP | 1 156 112 A1 | 11/2001 |
| WO | WO 98/34640 | 8/1998 |
| WO | WO 00/42560 | 7/2000 |
| WO | WO 01/16810 A2 | 3/2001 |
| WO | WO 02/29088 A2 | 4/2002 |

OTHER PUBLICATIONS

NAR's web pages, printed from http://nar.oxfordjournals.org/archive/2002.dtl on Jun. 21, 2010.*

Hoover David M et al: "DNAWorks: an automated method for designing oligonucleotides for PCR-based gene synthesis" Nucleic Acids Research, Oxford University Press, Surrey, GB, Bd. 30, Nr. 10, May 15, 2002.

Chrislaine Withers-Martinez et al: "PCR-based gene synthesis as an efficient approach for expression of the A+T-rich malaria genome" Protein Engineering, Oxford University Press, Surrey, GB, Bd. 12, Nr. 12, Dec. 1999.

Williams D P et al: "Design, Synthesis and Expression of a Human Interleukin-2 Gene Incorporating the Condon Usage Bias Found in Highly Expressed *Escherichia coli* Genes" Nucleic Acids Research, Oxford University Press, Surrey, GB, Bd. 16, Nr. 22, Nov. 25, 1988.

Lee F et al: "Isolation of Complementary DNA for a Human Granulocyte-Macrophage Colony-Stimulating Factor by Functional Expression in Mammalian Cells" Proceedings of the National Academy of Sciences of the United States of America, Bd. 82, Nr. 13, 1985.

Meazza R et al: "Identification of a novel interleukin-15 (IL-15) transcript isoform generated by alternative splicing in human small cell lung cancer cell lines." ONCOGENE. May 16, 1996, Bd. 12, Nr. 10.

Sinclair, G. & Choy, F.Y.: Synonymous codon usage bias and the expression of human glucocerebrosidase in the methylotrophic yeast, *Pichia pastoris*. Protein Expr. Purif. (Oct. 2002) 26 (1) 96-105.

Hamdan, F.F. et al.: Codon optimization improves heterologous expression of a *Schistosoma mansoni* cDNA in HEK293 cells. Parasitol. Res. (Jun. 2002) 88 (6) 583-6.

Deml, L. et al.: Multiple effects of codon usage optimization on expression and immunogenicity of DNA candidate vaccines encoding the human immunodeficiency virus type 1 Gag protein. J. Virol. (2001) 75 (22) 10991-1001.

Hale, R.S. & Thompson, G.: Codon optimization of the gene encoding a domain from human type 1 neurofibromin protein results in a threefold imporvement in expresion level in *Escherichia coli*. Protein Expr. Purif. (1998) 12 (2) 185-8.

Humphreys, D.P. et al.: High-level periplasmic expression in *Escherichia coli* using a eukaryotic signal peptide: importance of codon usage at the 5' end of the coding sequence. Protein Expr. Purif. (2000) 20 (2) 252-64.

Kim, C.H. et al.: Codon optimization for high-level expression of human erythropoietin (EPO) in mammalian cells. Gene (1977) 199 (1-2) 293-301.

* cited by examiner

*Primary Examiner* — Shubo Zhou

(57) ABSTRACT

The invention relates to a method for optimizing a nucleotide sequence for expression of a protein on the basis of the amino acid sequence of the protein, in which for a particular region there is specification of a test sequence with m optimization positions on which the codon occupation is varied, a quality function being used to ascertain the optimal codon occupation on these optimization positions, and one or more codons of this optimal occupation being specified as codons of the optimized nucleotide sequence. These steps are iterated, with the codons of the optimized nucleotide sequence which are specified in the preceding steps remaining unchanged in subsequent iteration steps. The invention additionally relates to a device for carrying out this method.

22 Claims, 17 Drawing Sheets

Human GM-CSF

Murine Gm-CSF

Human IL15

SEQUENCE LISTING

<160> NUMBER OF SEQ ID NOS: 32

<210> SEQ ID NO 1
<211> LENGTH: 435
<212> TYPE: DNA
<213> ORGANISM: Homo sapiens

<400> SEQUENCE: 1

| | | |
|---|---|---|
| atgtggctgc agagcctgct gctcttgggc actgtggcct gcagcatctc tgcacccgcc | 60 |
| cgctcgccca gccccagcac gcagccctgg gagcatgtga atgccatcca ggaggcccgg | 120 |
| cgtctcctga acctgagtag agacactgct gctgagatga atgaaacagt agaagtcatc | 180 |
| tcagaaatgt ttgacctcca ggagccgacc tgcctacaga cccgcctgga gctgtacaag | 240 |
| cagggcctgc ggggcagcct caccaagctc aagggcccct tgaccatgat ggccagccac | 300 |
| tacaagcagc actgccctcc aaccccggaa acttcctgtg caacccagat tatcaccttt | 360 |
| gaaagtttca agagaaacct gaaggacttt ctgcttgtca tcccctttga ctgctgggag | 420 |
| ccagtccagg agtag | 435 |

<210> SEQ ID NO 2
<211> LENGTH: 435
<212> TYPE: DNA
<213> ORGANISM: Homo sapiens

<400> SEQUENCE: 2

| | | |
|---|---|---|
| atgtggctgc agagcctgct gctgctggga acagtggcct gtagcatctc tgcccctgcc | 60 |
| agaagcccta gccctagcac acagccttgg gagcacgtga atgccatcca ggaggccagg | 120 |
| agactgctga acctgagcag agatacagcc gccgagatga acgagaccgt ggaggtgatc | 180 |
| agcgagatgt tcgacctgca ggagcctaca tgcctgcaga cccggctgga gctgtataag | 240 |
| cagggcctga gaggctctct gaccaagctg aagggccccc tgacaatgat ggccagccac | 300 |
| tacaagcagc actgccctcc taccccctgag acaagctgcg ccacccagat catcaccttc | 360 |
| gagagcttca aggagaacct gaaggacttc ctgctggtga tccccttcga ttgctgggag | 420 |
| cccgtgcagg agtag | 435 |

<210> SEQ ID NO 3
<211> LENGTH: 489
<212> TYPE: DNA
<213> ORGANISM: Homo sapiens

<400> SEQUENCE: 3

| | | |
|---|---|---|
| atgagaattt cgaaaccaca tttgagaagt atttccatcc agtgctactt gtgtttactt | 60 |
| ctaaacagtc attttctaac tgaagctggc attcatgtct tcattttggg ctgtttcagt | 120 |
| gcagggcttc ctaaaacaga agccaactgg gtgaatgtaa taagtgattt gaaaaaaatt | 180 |
| gaagatctta ttcaatctat gcatattgat gctactttat atacggaaag tgatgttcac | 240 |
| cccagttgca aagtaacagc aatgaagtgc tttctcttgg agttacaagt tatttcactt | 300 |
| gagtccggag atgcaagtat tcatgataca gtagaaaatc tgatcatcct agcaaacaac | 360 |
| agtttgtctt ctaatgggaa tgtaacagaa tctggatgca aagaatgtga ggaactggag | 420 |
| gaaaaaaata ttaaagaatt tttgcagagt tttgtacata ttgtccaaat gttcatcaac | 480 |
| acttcttag | 489 |

<210> SEQ ID NO 4

```
<211> LENGTH: 489
<212> TYPE: DNA
<213> ORGANISM: Homo sapiens

<400> SEQUENCE: 4
atgcggatca gcaagcccca cctgaggagc atcagcatcc agtgctacct gtgcctgctg      60
ctgaacagcc acttcctgac agaggccggc atccacgtgt ttatcctggg ctgcttctct     120
gccggcctgc ctaagacaga ggccaactgg gtgaacgtga tcagcgacct gaagaagatc     180
gaggacctga tccagagcat gcacatcgac gccaccctgt acacagagag cgacgtgcac     240
cctagctgta aggtgaccgc catgaagtgc ttcctgctgg agctgcaggt gatcagcctg     300
gagagcggcg atgccagcat ccacgacacc gtggagaacc tgatcatcct ggccaacaac     360
agcctgagca gcaacggcaa tgtgaccgag agcggctgca aggagtgtga ggagctggag     420
gagaagaaca tcaaggagtt cctgcagagc ttcgtgcaca tcgtgcagat gttcatcaac     480
accagctag                                                              489

<210> SEQ ID NO 5
<211> LENGTH: 426
<212> TYPE: DNA
<213> ORGANISM: Mus musculus

<400> SEQUENCE: 5
atgtggctgc agaatttact tttcctgggc attgtggtct acagcctctc agcacccacc      60
cgctcaccca tcactgtcac ccggccttgg aagcatgtag aggccatcaa gaagccctg      120 aacctcctgg atgacatgcc tgtcacattg aatgaagagg tagaagtcgt ctctaacgag     180
ttctccttca agaagctaac atgtgtgcag acccgcctga agatattcga gcagggtcta     240
cggggcaatt tcaccaaaac tcaagggcgcc ttgaacatga cagccagcta ctaccagaca    300
tactgccccc caactccgga aacggactgt gaaacacaag ttaccaccta tgcggatttc     360
atagacagcc ttaaaacctt tctgactgat atccccttg aatgcaaaaa accaggccaa      420
aaatag                                                                 426

<210> SEQ ID NO 6
<211> LENGTH: 426
<212> TYPE: DNA
<213> ORGANISM: Mus musculus

<400> SEQUENCE: 6
atgtggctgc agaacctgct gttcctgggc atcgtggtgt acagcctgag cgcccccacc      60
aggagcccca tcaccgtgac caggccctgg aagcacgtgg aggccatcaa ggaggccctg     120
aacctgctgg acgacatgcc cgtgaccctg aacgaggagg tggaggtggt gagcaacgag     180
ttcagcttca gaagctgac ctgcgtgcag accaggctga gatcttcga gcagggcctg       240 aggggcaact tcaccaagct gaaggcgcc ctgaacatga ccgccagcta ctaccagacc      300
tactgccccc ccaccccga gaccgactgc gagacccagg tgaccaccta cgccgacttc      360
atcgacagcc tgaagacctt cctgaccgac atccccttcg agtgcaagaa gcccggccag     420
aagtag                                                                 426

<210> SEQ ID NO 7
<211> LENGTH: 279
<212> TYPE: DNA
<213> ORGANISM: Mus musculus

<400> SEQUENCE: 7
```

```
atgaaggtct ccaccactgc ccttgctgtt cttctctgta ccatgacact ctgcaaccaa     60
gtcttctcag cgccatatgg agctgacacc ccgactgcct gctgcttctc ctacagccgg    120
aagattccac gccaattcat cgttgactat tttgaaacca gcagcctttg ctcccagcca    180
ggtgtcattt tcctgactaa gagaaaccgg cagatctgcg ctgactccaa agagacctgg    240
gtccaagaat acatcactga cctggaactg aatgcctag                           279
```

<210> SEQ ID NO 8
<211> LENGTH: 279
<212> TYPE: DNA
<213> ORGANISM: Mus musculus

<400> SEQUENCE: 8

```
atgaaggtga gcaccacagc tctggctgtg ctgctgtgca ccatgaccct gtgcaaccag     60
gtgttcagcg ctccttacgg cgccgatacc cctacagcct gctgcttcag ctacagcagg    120
aagatcccca ggcagttcat cgtggactac ttcgagacca gcagcctgtg ttctcagccc    180
ggcgtgatct tcctgaccaa gcggaacaga cagatctgcg ccgacagcaa ggagacatgg    240
gtgcaggagt acatcaccga cctggagctg aacgcctag                           279
```

<210> SEQ ID NO 9
<211> LENGTH: 42
<212> TYPE: DNA
<213> ORGANISM: Artificial Sequence
<220> FEATURE:
<223> OTHER INFORMATION: Optimal DNA sequence corresponding to
      hypothetical amino acid sequence.
<220> FEATURE:
<221> NAME/KEY: misc_feature
<222> LOCATION: (42)..(42)
<223> OTHER INFORMATION: n = a, t, g, or c

<400> SEQUENCE: 9

```
garcarttya thathaaraa yatgttyath athaaraayg cn                        42
```

<210> SEQ ID NO 10
<211> LENGTH: 14
<212> TYPE: PRT
<213> ORGANISM: Artificial Sequence
<220> FEATURE:
<223> OTHER INFORMATION: Hypothetical amino acid sequence.

<400> SEQUENCE: 10

```
Glu Gln Phe Ile Ile Lys Asn Met Phe Ile Ile Lys Asn Ala
1               5                   10
```

<210> SEQ ID NO 11
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 11

```
garcartty                                                              9
```

<210> SEQ ID NO 12
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

-continued

```
<400> SEQUENCE: 12 carttyath                                                                 9

<210> SEQ ID NO 13
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 13 ttyathath                                                                 9

<210> SEQ ID NO 14
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 14 athathaar                                                                 9

<210> SEQ ID NO 15
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 15 athaaraay                                                                 9

<210> SEQ ID NO 16
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 16 aaraayatg                                                                 9

<210> SEQ ID NO 17
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 17 aayatgtty                                                                 9

<210> SEQ ID NO 18
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 18
```

-continued

```
atgttyath                                                             9
```

<210> SEQ ID NO 19
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 19

```
ttyathath                                                             9
```

<210> SEQ ID NO 20
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 20

```
athathaar                                                             9
```

<210> SEQ ID NO 21
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.

<400> SEQUENCE: 21

```
athaaraay                                                             9
```

<210> SEQ ID NO 22
<211> LENGTH: 9
<212> TYPE: DNA
<213> ORGANISM: Artificial Sequence
<220> FEATURE:
<223> OTHER INFORMATION: Combination DNA Sequence for amino acid SEQ ID
      NO: 10.
<220> FEATURE:
<221> NAME/KEY: misc_feature
<222> LOCATION: (9)..(9)
<223> OTHER INFORMATION: n = a, t, g, or c

<400> SEQUENCE: 22

```
aaraaygcn                                                             9
```

<210> SEQ ID NO 23
<211> LENGTH: 238
<212> TYPE: PRT
<213> ORGANISM: Aequorea victoria
<300> PUBLICATION INFORMATION:
<308> DATABASE ACCESSION NUMBER: GenBank M62654
<309> DATABASE ENTRY DATE: 1993-04-26
<313> RELEVANT RESIDUES: (1)..(238)

<400> SEQUENCE: 23

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
```

```
                    50                    55                    60
Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Tyr Lys Asp Asp Gly Asn Tyr Lys Ser Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Gly Ile Thr His Gly Met Asp Glu Leu Tyr Lys
225                 230                 235

<210> SEQ ID NO 24
<211> LENGTH: 12
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (10)..(10)
<223> OTHER INFORMATION: n = a, t, g, or c

<400> SEQUENCE: 24
yyyyyyyyyn ag                                                           12

<210> SEQ ID NO 25
<211> LENGTH: 11
<212> TYPE: DNA
<213> ORGANISM: Artificial Sequence
<220> FEATURE:
<223> OTHER INFORMATION: Sequence motif

<400> SEQUENCE: 25
wwwatttaww w                                                            11

<210> SEQ ID NO 26
<211> LENGTH: 10
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (7)..(7)
<223> OTHER INFORMATION: n = a, t, g, or c

<400> SEQUENCE: 26 aaggagnatg                                                              10
```

```
<210> SEQ ID NO 27
<211> LENGTH: 10
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (7)..(7)
<223> OTHER INFORMATION: n = a, t, g, or c

<400> SEQUENCE: 27 aggaggnatg                                                          10

<210> SEQ ID NO 28
<211> LENGTH: 13
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (10)..(10)
<223> OTHER INFORMATION: n = a, t, g, or c

<400> SEQUENCE: 28
taasgaggtn dtg                                                      13

<210> SEQ ID NO 29
<211> LENGTH: 10
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (7)..(7)
<223> OTHER INFORMATION: n = a, t, g, or c

<400> SEQUENCE: 29 agagagnatg                                                          10

<210> SEQ ID NO 30
<211> LENGTH: 11
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (8)..(8)
<223> OTHER INFORMATION: n = a, t, g, or c

<400> SEQUENCE: 30
aaggaggnat g                                                        11

<210> SEQ ID NO 31
<211> LENGTH: 12
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (9)..(9)
<223> OTHER INFORMATION: n = a, t, g, or c

<400> SEQUENCE: 31
aacggaggna tg                                                       12
```

-continued

```
<210> SEQ ID NO 32
<211> LENGTH: 13
<212> TYPE: DNA
<213> ORGANISM: Artificial Sequence
<220> FEATURE:
<223> OTHER INFORMATION: Sequence motif
<220> FEATURE:
<221> NAME/KEY: misc_feature
<222> LOCATION: (10)..(10)
<223> OTHER INFORMATION: n = a, t, g, or c

<400> SEQUENCE: 32
aagaaggaan atg                                                          13
```

METHOD AND DEVICE FOR OPTIMIZING A NUCLEOTIDE SEQUENCE FOR THE PURPOSE OF EXPRESSION OF A PROTEIN

The invention relates generally to the production of synthetic DNA sequences and to the use thereof for producing proteins by introducing these DNA sequences into an expression system, for example into a host organism/a host cell or a system for in vitro expression, any of which expresses the appropriate protein. It relates in particular to methods in which a synthetic nucleotide sequence is optimized for the particular expression system, that is to say for example for an organism/for a host cell, with the aid of a computer.

One technique for the preparation and synthesis of proteins is the cloning and expression of the gene sequence corresponding to the protein in heterologous systems, e.g. *Escherichia coli* or yeast. Naturally occurring genes are, however, frequently suboptimal for this purpose. Since in a DNA sequence expressing a protein in each case one triplet of bases (codon) expresses one amino acid, it is possible for an artificial DNA sequence for expression of the desired protein to be synthesized and to be used for cloning and expression of the protein. One problem with this procedure is that a predefined amino acid sequence does not correspond to a unique nucleotide sequence. This is referred to as the degeneracy of the genetic code. The frequency with which different organisms use codons for expressing an amino acid differs (called the codon usage). There is ordinarily in a given organism one codon which is predominantly used and one or more codons which are used with comparatively low frequency by the organism for expressing the corresponding amino acid. Since the synthesized nucleotide sequence is to be used in a particular organism, the choice of the codons ought to be adapted to the codon usage of the appropriate organism. A further important variable is the GC content (content of the bases guanine and cytosine in a sequence). Further factors which may influence the result of expression are DNA motifs and repeats or inverse complementary repeats in the base sequence. Certain base sequences produce in a given organism certain functions which may not be desired within a coding sequence. Examples are cis-active sequence motifs such as splice sites or transcription terminators. The unintentional presence of a particular motif may reduce or entirely suppress expression or even have a toxic effect on the host organism. Sequence repeats may lead to lower genetic stability and impede the synthesis of repetitive segments owing to the risk of incorrect hybridizations. Inverse complementary repeats may lead to the formation of unwanted secondary structures at the RNA level or cruciform structures at the DNA level, which impede transcription and lead to genetic instability, or may have an adverse effect on translation efficiency.

A synthetic gene ought therefore to be optimized in relation to the codon usage and the GC content and, on the other hand, substantially avoid the problems associated with DNA motifs and sequence repeats and inverse complementary sequence repeats. These requirements cannot, however, ordinarily be satisfied simultaneously and in an optimal manner. For example, optimization to optimal codon usage may lead to a highly repetitive sequence and a considerable difference from the desired GC content. The aim therefore is to reach a compromise which is as optimal as possible between satisfying the various requirements. However, the large number of amino acids in a protein leads to a combinatorial explosion of the number of possible DNA sequences which—in principle—are able to express the desired protein. For this reason, various computer-assisted methods have been proposed for ascertaining an optimal codon sequence.

P. S. Sarkar and Samir K. Brahmachari, Nucleic Acids Research 20 (1992) 5713 describe investigations into the role of the choice of codons in the formation of certain spatial structures of a DNA sequence. This involved generation of all the possible degenerate nucleotide sequences. Assessment of the sequences in relation to the presence of structural motifs and to structure-forming segments was performed by a computer using a knowledge base. The use of a quality function is not disclosed.

D. M. Hoover and J. Lubkowski, Nucleic Acid Research 30 (2002), No. 10 e43 proposes a computer-assisted method in which the nucleotide sequence is divided into an odd number of segments for each of which a quality function (score) is calculated. The quality function includes inter alia the codon usage, the possibility of forming hairpin structures and the differences from the desired melting temperature. The value of the quality function for the complete sequence is determined from the total of the values of the quality function for the individual segments. The codon occupation within a segment is optimized by a so-called Monte-Carlo method. This entails random selection of codon positions in which the codon of an initial sequence is replaced by a randomly selected equivalent codon. At the same time, the limits of the segments are redefined in an iteration. In this way there is random generation of a complete gene sequence. If the value of the quality function for the complete sequence is less than the previous sequence, the new sequence is retained. If it is larger, the new sequence is retained with a certain probability, this probability being controlled by a Boltzmann statistic. If the sequence does not change during a predetermined number of iterations, this sequence is regarded as optimal sequence.

Random methods of this type have the disadvantage that they depend greatly on the choice of the convergence criteria.

It is the object of the invention to provide an alternative method for optimizing a nucleotide sequence for the expression of a protein on the basis of the amino acid sequence of the protein, which can be implemented with relatively little storage space and relatively little computing time on a computer, and which avoids in particular the disadvantages of the random methods.

This object is achieved according to the invention by a method for optimizing a nucleotide sequence for the expression of a protein on the basis of the amino acid sequence of the protein, which comprises the following steps carried out on a computer:

generation of a first test sequence of n codons which correspond to n consecutive amino acids in the protein sequence, where n is a natural number and is less than or equal to N, the number of amino acids in the protein sequence, specification of m optimization positions in the test sequence which correspond to the position of m codons, in particular of m consecutive codons, at which the occupation by a codon, relative to the test sequence, is to be optimized, where $m \leq n$ and m<N, generation of one or more further test sequences from the first test sequence by replacing at one or more of the m optimization positions a codon of the first test sequence by another codon which expresses the same amino acid, assessment of each of the test sequences with a quality function and ascertaining the test sequence which is optimal in relation to the quality function, specification of p codons of the optimal test sequence which are located at one of the m optimization positions, as result codons which form the codons of the optimized nucleotide sequence at the positions which corresponds to the position of said p codons in the test sequence, where p is a natural number and p≦m, iteration of the preceding steps, where in each iteration step the test sequence comprises the appropriate result codon at the positions which correspond to positions of specified result codons in the optimized nucleotide sequence, and the optimization positions are different from positions of result codons.

According to the preferred embodiment of the invention, the aforementioned steps are iterated until all the codons of the optimized nucleotide sequence have been specified, i.e. occupied by result codons.

Thus, the optimization according to the invention is not of the sequence as a whole but successively on part regions. The p result codons specified as optimal in one iteration step are not changed again in the subsequent iteration steps and, on the contrary, are assumed to be given in the respective optimization steps. It is preferred for the number of result codons which are specified in this way for further iterations and are treated as predefined to be smaller than the number m of optimization positions at which the codons are varied in an iteration step. In at least the majority of iteration steps and, in a particular embodiment, in all iteration steps apart from the first, in turn m is smaller than the number of codons of the test sequence (n). This makes it possible to take account not only of local effects on the m varied positions, but also of wider-ranging correlations, e.g. in connection with the development of RNA secondary structures.

According to the embodiments preferred at present, m is in the range from 3 to 20, preferably in the range from 5 to 10. With this choice of this parameter it is possible to vary the codons with an acceptable usage of storage and computing time and, at the same time, achieve good optimization of the sequence.

According to one embodiment, m need not be the same in the various iteration steps but, on the contrary, may also be different in different iteration steps. It is also possible to provide for variation of the test sequence for different values of m to be carried out in one iteration step and, where appropriate, for taking account only of the optimization result for one value of m, in order to reduce influences of the quantity m on the optimization result, and in order to check whether an increase in the number m leads to a change in the result.

According to the preferred embodiment, the m optimization positions or at least some of them are connected and thus form a variation window, on which the codon occupation is varied, in the test sequence.

The invention can in particular provide for some of the m optimization positions on which the codons are varied to be identical in two or more consecutive iteration steps. If the m positions are connected, this means that the variation window in one iteration step overlaps with the variation window of a preceding iteration step.

The invention can provide for the m optimization positions of the test sequences in one or more iteration steps to follow directly one or more result codons which have been specified as part of the optimized nucleotide sequence.

The invention can likewise provide for the p codons which are specified as result codons of the optimized nucleotide sequence in one or more iteration steps to be p consecutive codons which preferably directly follow one or more result codons which have been specified as part of the optimized nucleotide sequence in an earlier step.

The invention can provide for the nucleotide sequence to be optimized from one of its ends. In particular, the invention can provide for an increase in each iteration step of the length of the test sequence of the previous iteration step by a particular number of codons, which may be different in different iterations, until n=N. If n=N and the number of positions in the test sequence not occupied by result codons is smaller than or equal to the value of m used in the preceding iterations, or if this number on use of different values of m in different iterations is in the region of the values of m in question, it is possible to set p=m in the corresponding iteration step, where m is at the same time the number of codons not yet specified. The occupation which is found to be optimal for the optimization positions is then accepted for the result codons at these optimization positions. This applies in particular when a test sequence is generated for every possible combination of occupations of the optimization positions.

However, it is also possible to provide for the region of the test sequence within the complete sequence in one iteration step not, or not completely, to include the region of a test sequence in a previous iteration step. For example, the test sequence itself may form a window on the complete sequence, e.g. a window of fixed length, which window is shifted on the complete sequence during the various iterations.

According to a preferred embodiment, the test sequence is extended after each step by p codons, it being possible in particular for m to be constant for all iteration steps.

In analogy to the embodiment of the invention described above, it is also possible to provide for the nucleotide sequence to be optimized from a site in its interior. This can take place for example in such a way that an initial test sequence corresponding to a region in the interior of the nucleotide sequence to be optimized is initially enlarged successively on one side until the end of the nucleotide sequence to be optimized or another predefined point is reached on the nucleotide sequence to be optimized, and then the test sequence is enlarged towards the other side until the other end of the nucleotide sequence to be optimized or another predetermined point is reached there on the nucleotide sequence to be optimized.

The invention can also provide for the test sequences in one iteration step to consist of an optimized or otherwise specified partial sequence of length q and two variation regions which are connected on both sides thereof and have a length of respectively $m_1$ and $m_2$ codons, where $q+m_1+m_2=n$. The occupation of the variation regions can be optimized for both variation regions together by simultaneously varying and optimizing the codons on the $m_1$ and $m_2$ locations. It is preferred in such a case for $p_1$ and $p_2$ codons in the first and second variation region, which are used as given basis for the further iteration, to be specified in each iteration step. However, it is also possible to provide for the two variation regions to be varied and optimized independently of one another. For example, it is possible to provide for the occupation to be varied in only one of the two variation regions, and for codons to be specified only in the one region, before the variation and optimization in the second region takes place. In this case, the $p_1$ specified codons in the first region are assumed as given in the optimization of the second region. This procedure is worthwhile when small correlations at the most are to be expected between the two regions.

According to this embodiment, it is possible to provide for the nucleotide sequence to be optimized starting from a point or a region in the interior of the sequence.

The invention can provide in particular for the region of the test sequence on the complete sequence in each iteration step to include the region of the test sequences in all the preceding iteration steps, and for the region of a test sequence in at least some of the preceding iteration steps to be located in each case in the interior or in each case at the border of the region of the test sequence in the current iteration step.

The invention can provide for the nucleotide sequence to be optimized independently on different part regions. The optimized nucleotide sequence can then be the combination of the different optimized partial sequences. It is also possible to provide for at least some of the respective result codons from two or more optimized part regions to be used as constituent of a test sequence in one or more iterations.

A preferred embodiment of the invention provides for test sequences with all possible codon occupations for the m optimization positions to be generated in one iteration step from the first test sequence, and the optimal test sequence to be ascertained from all possible test sequences in which a codon at one or more of the m optimization positions has been replaced by another codon which expresses the same amino acid.

According to one embodiment of the invention, the quality function used to assess the test sequences is the same in all or at least the majority of the iterations. The invention may, however, also provide for different quality functions to be used in different iterations, for example depending on the length of the test sequences.

The method of the invention may comprise in particular the following steps:
  assessment of each test sequence with a quality function,
  ascertaining of an extreme value within the values of the quality function for all partial sequences generated in an iteration step,
  specification of p codons of the test sequence which corresponds to the extremal value of the weight function as result codons at the appropriate positions, where p is a natural number and $p \leq m$.

The quality function can be defined in such a way that either a larger value of the quality function means that the sequence is nearer the optimum, or a smaller value means that it is nearer the optimum. Correspondingly, the maximum or the minimum of the quality function among the generated codon sequences will be ascertained in the step of ascertaining the extreme value.

The invention can provide for the quality function to take account of one or more of the following criteria: codon usage for a predefined organism, GC content, sequence motifs, repetitive sequences, secondary structures, inverse repeats.

The invention can provide in particular for the quality function to take account of one or more of the following criteria:
  cis-active sequence motifs, especially DNA/protein interaction binding sites and RNA/protein interaction binding sites, preferably splice motifs, transcription factor binding sites, transcription terminator binding sites, polyadenylation signals, endonuclease recognition sequences, immunomodulatory DNA motifs, ribosome binding sites, recognition sequences for recombination enzymes, recognition signals for DNA-modifying enzymes, recognition sequences for RNA-modifying enzymes, sequence motifs which are underrepresented in a predefined organism.

The invention can also provide for the quality function to take account of one or more of the following criteria:
  exclusion or substantial exclusion of inverse complementary sequence identities of more than 20 nucleotides to the transcriptome of a predefined organism,
  exclusion or substantial exclusion of homology regions of more than 1000 base pairs, preferably 500 base pairs, more preferably 100 base pairs, to a predefined DNA sequence, for example to the genome of predefined organism or to the DNA sequence of a predefined vector construct.

The first of the two criteria relates to the exclusion of the mechanism known as RNA indifference, with which an organism eliminates or deactivates RNA sequences with more than 20 nucleotides exactly identical to another RNA sequence. The intention of the second criterion is to prevent the occurrence of recombination, that is to say incorporation of the sequence into the genetic material of the organism, or mobilization of DNA sequences through recombination with other vectors. Both criteria can be used as absolute exclusion criteria, i.e. sequences for which one or both of these criteria are satisfied are not taken into account. The invention can also provide, as explained in more detail below in connection with sequence motifs, for these criteria to be assigned a weight which in terms of contribution is larger than the largest contribution of criteria which are not exclusion criteria to the quality function.

The invention can also, where appropriate together with other criteria, provide the criterion that no homology regions showing more than 90% similarity and/or 99% identity to a predefined DNA sequence, for example to the appropriate genome sequence of the predefined organism or to the DNA sequence of a predefined vector construct, are generated. This criterion can also be implemented either as absolute exclusion criterion or in such a way that it makes a very large contribution, outweighing the contribution of other criteria which are not exclusion criteria, to the quality function.

It is possible to provide in particular for the quality function to be a function of various single terms, in particular a total of single terms, which in each case assess one criterion from the following list of criteria:
codon usage for a predefined organism, GC content, DNA motifs, repetitive sequences, secondary structures, inverse repeats.

Said function of single terms may be in particular a linear combination of single terms or a rational function of single terms. The criteria mentioned need not necessarily be taken completely into account in the weight function. It is also possible to use only some of the criteria in the weight function.

The various single terms in said function are called criterion weights hereinafter.

The invention can provide for the criterion weight relating to the codon usage (CU score) to be proportional to $\Sigma_i f_{ci}/f_{cmaxi}$, where
  $f_{ci}$ is the frequency of the codon placed at site i of the test sequence for the relevant organism to express the amino acid at site i in the amino acid sequence of the protein to be expressed, and
  $f_{cmaxi}$ is the frequency of the codon which expresses most frequently the amino acid at site i in the corresponding organism.

The measure $f_{ci}/f_{cmaxi}$ is known as the relative adaptiveness (cf. P. M. Sharp, W. H. Li, Nucleic Acids Research 15 (3) (1987), 1281 to 1295).

The local weight of the most frequently occurring codon is in this case, irrespective of the absolute frequency with which this codon occurs, set at a particular value, for example 1. This avoids the positions at which only a few codons are available for selection making a greater contribution to the total weight than those at which a larger number of codons are available for selection for expression of the amino acid. The index i may run over the entire n codons of the test sequence or a part thereof. In particular, it is possible to provide in one embodiment for i to run only over the m codons of the optimization positions.

The invention can provide for the criterion weight relating to the codon usage to be used only for the m ordering positions.

It is possible to use instead of the relative adaptiveness also the so-called RSCU (relative synonymous codon usage; cf. P. M. Sharp, W. H. Li, loc. cit.). The RSCU for a codon position is defined by $$RSCU_{ci} = f_{ci} d_i / (\Sigma_c f_{ci})$$

where the sum in the denominator runs over all the codons which express the amino acid at site i, and where $d_i$ indicates the number of codons which express said amino acid. In order to define a criterion weight on the basis of the RSCU it is possible to provide for the RSCU to be summed for the respective test sequence over all the codons of the test sequence or a part thereof, in particular over the m codons of the optimization positions. The difference from the criterion weight derived from the relative adaptiveness is that with this weighting each codon position is weighted with the degree of degeneracy, $d_i$, so that positions at which more codons are available for selection participate more in the criterion weight than positions at which only a few codons or even only a single codon are available for selection.

With the criterion weights described above for the codon usage, the arithmetic mean was formed over the local weights (relative adaptiveness, RSCU).

It can also be provided for the criterion weight relating to the codon usage to be proportional to the geometric mean of the local relative adaptiveness or the local RSCU, so that the following therefore applies $$CUScore = K(\Pi_i RSCU_i)^{1/L}$$

or $$CUScore = K(\Pi_i f_{ci}/f_{cmaxi})^{1/L}$$

where K is a scaling factor, and L is the number of positions over which the product is formed. Once again, it is possible in this case to form the product over the complete test sequence or a part, in particular over the m optimization positions.

In this connection, the invention also provides a method for optimizing a nucleotide sequence for expression of a protein on the basis of the amino acid sequence of the protein, which comprises the following steps carried out on a computer:
- generation of one or more test sequences of n codons which correspond to n consecutive amino acids in the protein sequence, where n is a natural number less than or equal to N, the number of amino acids in the protein sequence,
- assessment of the one or more test sequences on the basis of a quality function which comprises a geometric or arithmetic mean of the relative adaptiveness or of the RSCU over a number of L codon positions, where L is less than or equal to N,
- generation of one or more new test sequences depending on the result of said assessment.

It is moreover possible for the generation of one or more new test functions in the manner described above to take place in such a way that the new test sequences comprise a particular number of result codons specified on the basis of the preceding iterations but, for example, also in such a way that a particular test sequence is used with a particular probability, which depends on the value of the quality function, as basis for further iterations, in particular the further generation of test sequences, as is the case with Monte-Carlo methods.

Whereas the quality of a codon in the abovementioned methods is defined through the frequency of use in the transcriptome or a gene reference set of the expression organism, the quality of a particular codon can also alternatively be described by the biophysical properties of the codon itself. Thus, for example, it is known that codons with an average codon-anticodon binding energy are translated particularly efficiently.

It is therefore possible to use as measure of the translational efficiency of a test sequence for example the P2 index which indicates the ratio of the frequency of codons with average binding energy and codons with extremely strong or weak binding energy. It is also possible alternatively to utilize data obtained experimentally or by theoretical calculations for the translational efficiency or translation accuracy of a codon for the quality assessment. The abovementioned assessment criteria may be advantageous especially when the tRNA frequencies of the expression system need not be taken into account, because they can be specified by the experimenter as, for example, in in vitro translation systems.

The invention can provide for the criterion weight relating to the GC content (GCScore) to be a function of the contribution of the difference of the ascertained GC content of the partial sequence, GCC, to the optimal GC content, $GCC_{opt}$, where the GG content means the relative proportion of guanine and cytosine, for example in the form of a particular percentage proportion.

The criterion weight GCScore can have the following form, in particular:

$$GCScore = |\overline{GCC} - GCC_{opt}|^g \cdot h$$

where
$\overline{GCC}$ is the actual GC content of the test sequence or of a predetermined part of the test sequence, GCC, or the average GC content of the test sequence or of a predetermined part of the test sequence, <GCC>,
$GCC_{opt}$ is the desired (optimal) GC content,
g is a positive real number, preferably in the range from 1 to 3, in particular 1.3,
h is a positive real number.

The factor h is essentially a weighting factor which defines the relative weight of the criterion weight GCScore vis-à-vis the other criterion weights. Preferably, h is chosen so that the amount of the maximally achievable value of GCScore is in a range from one hundredth of up to one hundred times another criterion weight, in particular all criterion weights which represent no exclusion condition, such as, for example, the weights for a wanted or unwanted sequence motif.

To determine the average GC content it is possible to provide for a local GC content relating to a particular base position to be defined by the GC content on a window which was a particular size and which comprises this base and which, in particular, can be centered on this base. This local GC content is then averaged over the test sequence or a part region of the test sequence, in particular over the m optimization positions, it being possible to use both an arithmetic mean and a geometric mean here too. On use of an average GC content defined in this way there are fewer variations between test sequences differing in length n.

The invention can provide for the GC content to be ascertained over a window which is larger than the region of the m optimization positions and includes this. If the optimization positions form a coherent variation window it is possible to provide for b bases before and/or after the variation window to be included in the determination of the criterion weight for the GC content (GCScore), where b can be in a range from 15 to 45 bases (corresponding to 5 to 15 codons), preferably in a range from 20 to 30 bases.

The invention can further provide, inasmuch as the quality function is maximized, for a fixed amount to be subtracted for each occurrence of a sequence motif which is not permitted or is unwanted, and for a fixed amount to be added for each wanted or required motif, when ascertaining the value of the quality function (and vice versa for minimization of the quality function). This amount for unwanted or required motifs can be distinctly larger than all other criterion weights, so that the other criteria are unimportant compared therewith. An exclusion criterion is achieved thereby, while at the same time there is differentiation according to whether a motif has occurred once or more than once. However, it is likewise possible to define a worthwhile quality function and carry out an assessment of the test sequences with the quality function even if the condition relating to the sequence motif (non-presence of a particular motif/presence of a particular motif) cannot be satisfied for all test sequences produced in an iteration step. This will be the case in particular when the length n of the test sequences is relatively small compared with N, because a particular motif can often occur only when n is relatively large, because of the predefined amino acids of the protein sequence.

The invention can further provide for the complete test sequence or part thereof to be checked for whether particular partial sequence segments or sequence segments similar to particular partial sequence segments occur in another region of the test sequence or of a given region of the test sequence or whether particular partial sequence segments or sequence segments similar to particular partial sequence segments occur in the inverse complementary test sequence or part of the inverse complementary test sequence, and for a criterion weight for sequence repeats (repeats) and/or inverse sequence repeats (inverse repeats) to be calculated dependent thereon.

Ordinarily, the sequence will be checked not only for whether a particular sequence segment is present identically in the test sequence or the inverse complementary test sequence or of a part region thereof, but also for whether a similar, i.e. only partially matching, sequence is present in the test sequence or the inverse complementary test sequence or of a part thereof. Algorithms for finding global matches (global alignment algorithms) or local matches (local alignment algorithms) of two sequences are generally known in bioinformatics. Suitable methods include, for example, the dynamic programming algorithms generally known in bioinformatics, e.g. the so-called Needleman-Wunsch algorithm for global alignment and the Smith-Waterman algorithm for local alignment. In this regard, reference is made for example to Michael S. Waterman, Introduction to Computational Biology, London, New York 2000, especially pages 207 to 209 or Dan Gusfield, Algorithms on Strings, Trees and Sequences, Cambridge, 1999, especially pages 215 to 235.

The invention can in particular provide for every repeat of a partial sequence segment in another part of the test sequence or of a predefined region of the test sequence to be weighted with a particular weight which represents a measure of the degree of match and/or the size of the mutually similar segments, and for the weights of the individual repeats to be added to ascertain the criterion weight relating to the repeats or inverse complementary repeats. It is likewise possible to provide for the weights of the individual repeats to be exponentiated with a predefined exponent whose value is preferably between 1 and 2, and then for the summation to ascertain the criterion weight relating to the repeats or inverse complementary repeats to be carried out. It is moreover possible to provide for repeats below a certain length and/or repeats whose weight fraction is below a certain threshold not to be taken into account. The invention can provide, for the calculation of the appropriate criterion weight, for account to be taken only of the repeats or inverse complementary repeats of a partial sequence segment which is located in a predefined part region of the test sequence (test region), e.g. at its end and/or in a variation window. It is possible to provide for example for only the last 36 bases of the test sequence to be checked for whether a particular sequence segment within these 36 bases matches with another sequence segment of the complete test sequence or of the complete inverse complementary test sequence.

The invention can provide for only the segment or the M segments of the test sequence which provide the largest, or largest in terms of amount, contribution to the criterion weight, where M is a natural number, preferably between 1 and 10, to be taken into account in the criterion weights relating to repeats, inverse complementary repeats and/or DNA motifs.

According to one embodiment of the invention, it is possible to provide for generation of a matrix whose number of columns corresponds to the number of positions of the region of the test sequence (test region) which is to be checked for repeats in other regions, and whose number of rows corresponds to the number of positions of the region of the test sequence with which comparison is intended (comparison region). Both the test region and the comparison region may include the complete test sequence.

The invention can further provide for the total weight function TotScore to be determined as follows:

$$TotScore = CUScore - GCScore - REPScore - SiteScore$$

where CUScore is the criterion weight for the codon usage, GCScore is the criterion weight for the GC content, REPScore is the criterion weight for repeats and inverse complementary repeats of identical or similar sequence segments, and SiteScore is the criterion weight for the occurrence of unwanted or required motifs.

The weight REPScore can, according to one embodiment of the invention, consist of a sum of two components, of which the first indicates the criterion weight for the repeat of identical or similar sequence segments in the test sequence itself or of a part region thereof, and the second component indicates the criterion weight for inverse complementary repeats of identical or similar sequence segments in the test sequence or of a part region thereof.

If the quality function is composed of portions of a plurality of test criteria, especially when the quality function consists of a linear combination of criterion weights, a test sequence need not necessarily be assessed according to all criteria in an iteration step. On the contrary, the assessment can be stopped as soon as it is evident that the value of the quality function is less or, speaking more generally, less optimal than the value of the quality function of a test sequence which has already been assessed. In the embodiments described previously, most of the criteria, such as the criterion weights for repetitive elements, motifs to be excluded etc., are included negatively in the quality function. If, after calculating the criterion weights which are included positively in the quality function and, where appropriate, some of the criterion weights which are included negatively in the quality function, the summation corresponding to the linear combination, defined by the quality function, of the appropriate previously calculated criterion weights gives a value which is smaller than a previously calculated value of the complete quality function for another test sequence, the currently assessed test sequence can be eliminated at once. It is likewise frequently possible, for example when a criterion weight is considerably larger in terms of amount than all the other weights, for the assessment to be stopped at once after ascertaining the corresponding criterion weight. If, for example, an unwanted motif has not appeared in a first test sequence, and the unwanted motif appears in a second test sequence, the second test sequence can be immediately excluded, because the criterion weight for the motif search is so large that it cannot be compensated by other criterion weights.

The invention can provide in particular in embodiments in which the quality function can be calculated iteratively for there to be, in at least one iteration, determination of an upper (or in the case of optimization to the minimum of the quality function lower) limit below (or above) which the value of the complete quality function lies, and for the iteration of the quality function to be stopped when this value is below (or above) the value which has previously been ascertained for the complete quality function for a test sequence.

The invention can provide in these cases for said upper or lower limit to be used if necessary as value of the quality function in the further method for this test sequence, and/or for the corresponding test sequence to be eliminated in the algorithm, for example through the variable for the optimized test sequence remaining occupied by a previously found test sequence for which the quality function a higher value than the abovementioned limit, and the algorithm to go on to the assessment of the next test sequence. The invention can moreover, especially when the quality function is a linear combination of criterion weights, provide for calculation in the first iterations of that contribution or those contributions whose highest value or whose minimal value has the highest absolute value.

The invention can provide in the case of a quality function which is optimized to its maximum and which is formed by a linear combination of criterion weights for firstly the positive portions of the linear combination to be calculated and the iteration to be stopped when, in one iteration after the calculation of all positive criterion weights, the value of the quality function in this iteration is smaller than the value of the complete quality function for another test sequence.

The invention can also provide for an iteration of the quality function to be stopped when it is found in an iteration that the sum of the value of the quality function calculated in this iteration and the maximum value of the contribution of the as yet uncalculated criterion weights is below the value of the complete quality function of another test sequence.

The method of the invention may include the step of synthesizing the optimized nucleotide sequence.

It is possible to provide in this connection for the step of synthesizing the optimized nucleotide sequence to take place in a device for automatic synthesis of nucleotide sequences, for example in an oligonucleotide synthesizer, which is controlled by the computer which optimizes the nucleotide sequence.

The invention can provide in particular for the computer, as soon as the optimization process is complete, to transfer the ascertained data concerning the optimal nucleotide sequence to an oligonucleotide synthesizer and cause the latter to carry out the synthesis of the optimized nucleotide sequence.

This nucleotide sequence can then be prepared as desired. The protein is expressed by introducing the appropriate nucleotide sequence into host cells of a host organism for which it is optimized and which then eventually produces the protein.

The invention also provides a device for optimizing a nucleotide sequence for the expression of a protein on the basis of the amino acid sequence of the protein, which has a computer unit which comprises:

a unit for generation of a first test sequence of n codons which correspond to n consecutive amino acids in the protein sequence, where n is a natural number less than or equal to N, the number of amino acids in the protein sequence, a unit for specification of m optimization positions in the test sequence which correspond to the position of m codons at which the occupation by a codon, relative to the test sequence, is to be optimized, where $m \leqq n$ and $m<M$, a unit for generation of one or more further test sequences from the first test sequence by replacing at one or more of the m optimization positions a codon of the first test sequence by another codon which expresses the same amino acid, a unit for assessment of each of the test sequences with a quality function and for ascertaining the test sequence which is optimal in relation to the quality function, a unit for specification of p codons of the optimal test sequence which are located at one of the m optimization positions, as result codons which form the codons of the optimized nucleotide sequence at the positions which correspond to the positions of said p codons in the test sequence, where p is a natural number and $p \leqq m$, a unit for iteration of the steps of generation of a plurality of test functions, of assessment of the test sequences and of specification of result codons, preferably until all the codons of the optimized nucleotide sequence have been specified, where in each iteration step the test sequence comprises the appropriate result codon at the positions which correspond to positions of specified result codons in the optimized nucleotide sequence, and the optimization positions are different from positions of result codons.

The aforementioned units need not be different but may, in particular, be implemented by a single device which implements the functions of the aforementioned units.

The device of the invention may generally have a unit for carrying out the steps of the methods described above.

The device of the invention may have an oligonucleotide synthesizer which is controlled by the computer so that it synthesizes the optimized nucleotide sequence.

In this embodiment of the invention, the optimized nucleotide sequence can be synthesized either automatically or through an appropriate command from the user, without data transfers, adjustment of parameters and the like being necessary.

The invention also provides a computer program which comprises program code which can be executed by a computer and which, when it is executed on a computer, causes the computer to carry out a method of the invention.

The program code can moreover, when it is executed on a computer, cause a device for the automatic synthesis of nucleotide sequences to prepare the optimized nucleotide sequence.

The invention also provides a computer-readable data medium on which a program of the invention is stored in computer-readable form.

The invention further provides a nucleic acid which has been or can be prepared by a method of the invention, and a vector which comprises such a nucleic acid. The invention further provides a cell which comprises such a vector or such a nucleic acid, and a non-human organism or a non-human life form which comprises such a cell, it also being possible for such a non-human life form to be mammal.

Whereas in random methods there is no correlation between a sequence in a preceding iteration step and the sequence in a subsequent iteration step, there is according to the invention new specification of a codon in each iteration step. Since the test sequence is varied on only part of the complete sequence, the method can be carried out with less effort. It is possible in particular to evaluate all possible combinations of codons in the variation region. The invention makes use in an advantageous manner of the circumstance that long-range correlations within a nucleotide sequence are of minor importance, i.e. that to achieve an acceptable optimization result it is possible to vary the codons at one position substantially independently of the codons at a more remote position.

The method of the invention makes it possible to a greater extent than previous methods for relevant biological criteria to be included in the assessment of a test sequence. For example, with the method of the invention it is possible to take account of wanted or unwanted motifs in the synthetic nucleotide sequence. Since in a motif search even an individual codon may be crucial for whether a particular motif is present or not, purely stochastic methods will provide optimized sequences which comprise a required motif only with a very low probability or not at all. However, this is possible with the method of the invention because all codon combinations are tested over a part region of the sequence. It is possible where appropriate in order to ensure the presence or non-presence of a particular sequence motif to make the number m of optimization positions so large that it is larger than the number of codon positions (or the number of base positions divided by 3) of the corresponding motif. If the m optimization positions are connected, it is thus ensured that the occurrence of a particular sequence motif can be reliably detected and the corresponding motif can be ensured in the sequence or excluded from the latter. The numerical calculation of the quality function has particular advantages on use of weight matrix scans. Since in this case a different level of importance for recognition or biological activity can be assigned to the different bases of a recognition sequence, it is possible in the method of the invention, in which all possible codon combinations are tested over a part region of the sequence, to find the sequence which, for example, switches off most effectively a DNA motif by eliminating the bases which are most important for the activity, or it is possible to find an optimized compromise solution with inclusion of other criteria.

The invention is not in principle restricted to a particular organism. Organisms for which an optimization of a nucleotide sequence for expression of a protein using the method of the invention is of particular interest are, for example, organisms from the following groups:

viruses, especially vaccinia viruses,
prokaryotes, especially *Escherichia coli, Caulobacter cresentus, Bacillus subtilis, Mycobacterium* spec.,
yeasts, especially *Saccharomyces cerevisiae, Schizosaccharomyces pombe, Pichia pastoris, Pichia angusta*,
insects, especially *Sprodoptera frugiperda, Drosophila* spec.,
mammals, especially *Homo sapiens, Macaca mulata, Mus musculus, Bos taurus, Capra hircus, Ovis aries, Oryctolagus cuniculus, Rattus norvegicus*, Chinese hamster ovary,
monocotyledonous plants, especially *Oryza sativa, Zea mays, Triticum aestivum*,
dicotyledonous plants, especially *Glycin max, Gossypium hirsutum, Nicotiana tabacum, Arabidopsis thaliana, Solanum tuberosum*.

Proteins for which an optimized nucleotide sequence can be generated using the method of the invention are, for example:

enzymes, especially polymerases, endonucleases, ligases, lipases, proteases, kinases, phosphatases, topoisomerases,
cytokines, chemokines, transcription factors, oncogenes,
proteins from thermophilic organisms, from cryophilic organisms, from halophilic organisms, from acidophilic organisms, from basophilic organisms,
proteins with repetitive sequence elements, especially structural proteins,
human antigens, especially tumor antigens, tumor markers, autoimmune antigens, diagnostic markers,
viral antigens, especially from HAV, HBV, HCV, HIV, SIV, FIV, HPV, rinoviruses, influenza viruses, herpesviruses, poliomaviruses, hendra virus, dengue virus, AAV, adenoviruses, HTLV, RSV,
antigens of protozoa and/or disease-causing parasites, especially those causing malaria, leishmania; trypanosoma, toxoplasmas, amoeba,
antigens of disease-causing bacteria or bacterial pathogens, especially of the genera *Chlamydia, staphylococci, Klebsiella, Streptococcus, Salmonella, Listeria, Borrelia, Escherichia coli*,
antigens of organisms of safety level L4, especially *Bacillus anthracis*, Ebola virus, Marburg virus, poxviruses.

The preceding list of organisms and proteins for which the invention is used is by no means restrictive and is intended merely as example for better illustration.

Further features and advantages of the invention are evident from the following description of exemplary embodiments of the invention with reference to the appended drawings.

According to a preferred embodiment of the invention, in one iteration the choice of the codon for the ith amino acid of an amino acid sequence of length N is considered. For this purpose, all possible codon combinations of the available codons for the amino acids at positions i to i+m−1 are formed. These positions form a variation window and specify the optimization positions at which the sequence is to be varied. Every combination of codons on this variation window results in a DNA sequence with 3 m bases, which is called combination DNA sequence (CDS) hereinafter. In each iteration step, a test sequence which comprises the CDS at its end is formed for each CDS. In the first iteration step, the test sequences consist only of the combination DNA sequences. The test sequences are weighted with a quality function which is described in detail below, and the first codon of the CDS which exhibits the maximum value of the quality function is retained for all further iterations as codon of the optimized nucleotide sequence (result codon). This means that when the ith codon has been specified in an iteration, each of the test sequences comprises in the next iteration this codon at position i, and the codons of the various combination DNA sequences at positions i+1 to i+m. Thus, in the jth iteration, all test sequences consist at positions 1 to j−1 of the codons found to be optimal in the preceding iterations, while the codons at positions j to j+m−1 are varied. The quality of the DNA sequence can be expressed as criterion weight (individual score) for each individual test criterion. A total weight (total score) is formed by adding the criterion weights weighted according to specifications defined by the user and indicates the value of the quality function for the complete test sequence. If j=N−m+1, the optimal test sequence is at the same time the optimized nucleotide sequence according to the method of the invention. All the codons of the optimal CDS in this (last) step are therefore specified as codons of the optimized nucleotide sequence.

Figure 1A:
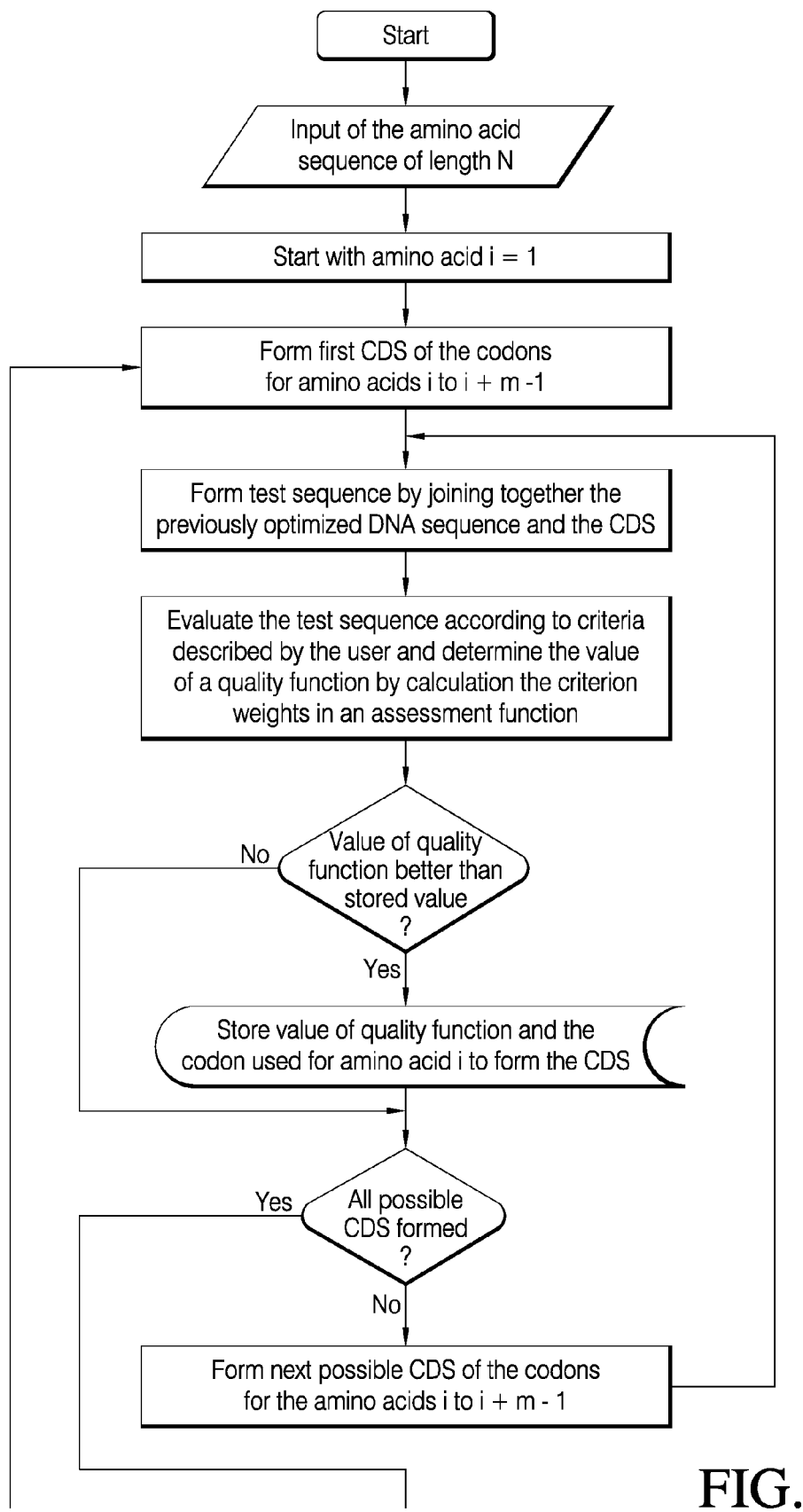
FIGS. 1a, 1b show a flow diagram of an exemplary embodiment of the method of the invention.
Figure 1B:
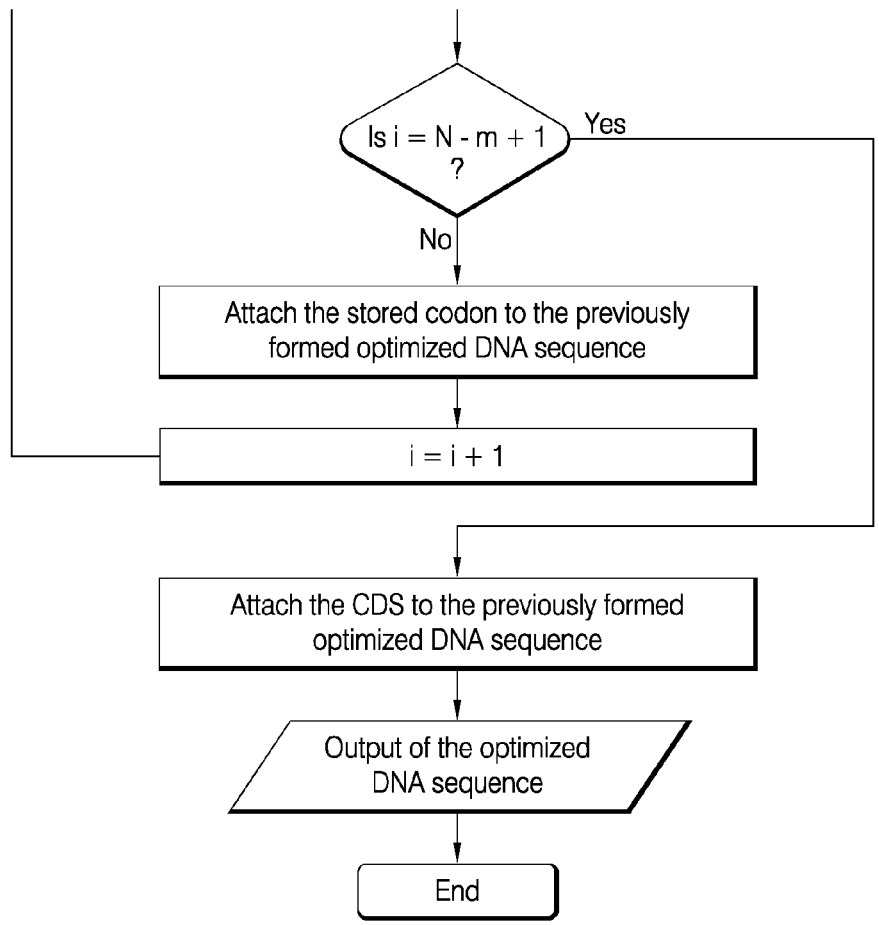

The procedure described above is illustrated diagrammatically in FIG. 1. The algorithm starts at the first amino acid (i=1). A first CDS of the codons for amino acids i to i+m−1 is then formed (in the first iteration, these are amino acids 1 to m). This CDS is combined with the previously optimized DNA sequence to give a test sequence. In the first step, the optimized DNA sequence consists of 0 elements. The test sequence therefore consists in the first iteration only of the previously formed (first) CDS.

The test sequence is then evaluated according to criteria defined by the user. The value of a quality function is calculated by criterion weights being calculated for various assessment criteria and being calculated in an assessment function. If the value of the quality function is better than a stored value of the quality function, the new value of the quality function is stored. At the same time, the first codon of the relevant CDS which represents amino acid i is also stored. If the value of the quality function is worse than the stored value, no action is taken. The next step is to check whether all possible CDS have been formed. If this is not the case, the next possible CDS is formed and combined with the previously optimized DNA sequence to give a new test sequence. The steps of evaluating, determining a quality function and comparing the value of the quality function with a stored value are then repeated. If, on the other hand, all possible CDS have been formed, and if i≈N−m+1, the stored codon is attached at position i to the previously formed optimized DNA sequence. In the first iteration, the optimized DNA sequence is formed by putting the stored codon on position 1 of the optimized DNA sequence. The process is then repeated for the next amino acid (i+1). If, on the other hand, i=N−m+1, the complete CDS of the optimal test sequence is attached to the optimized DNA sequence previously formed, because it is already optimized in relation to the assessment criteria. Output of the optimized sequence then follows.

Figure 2:
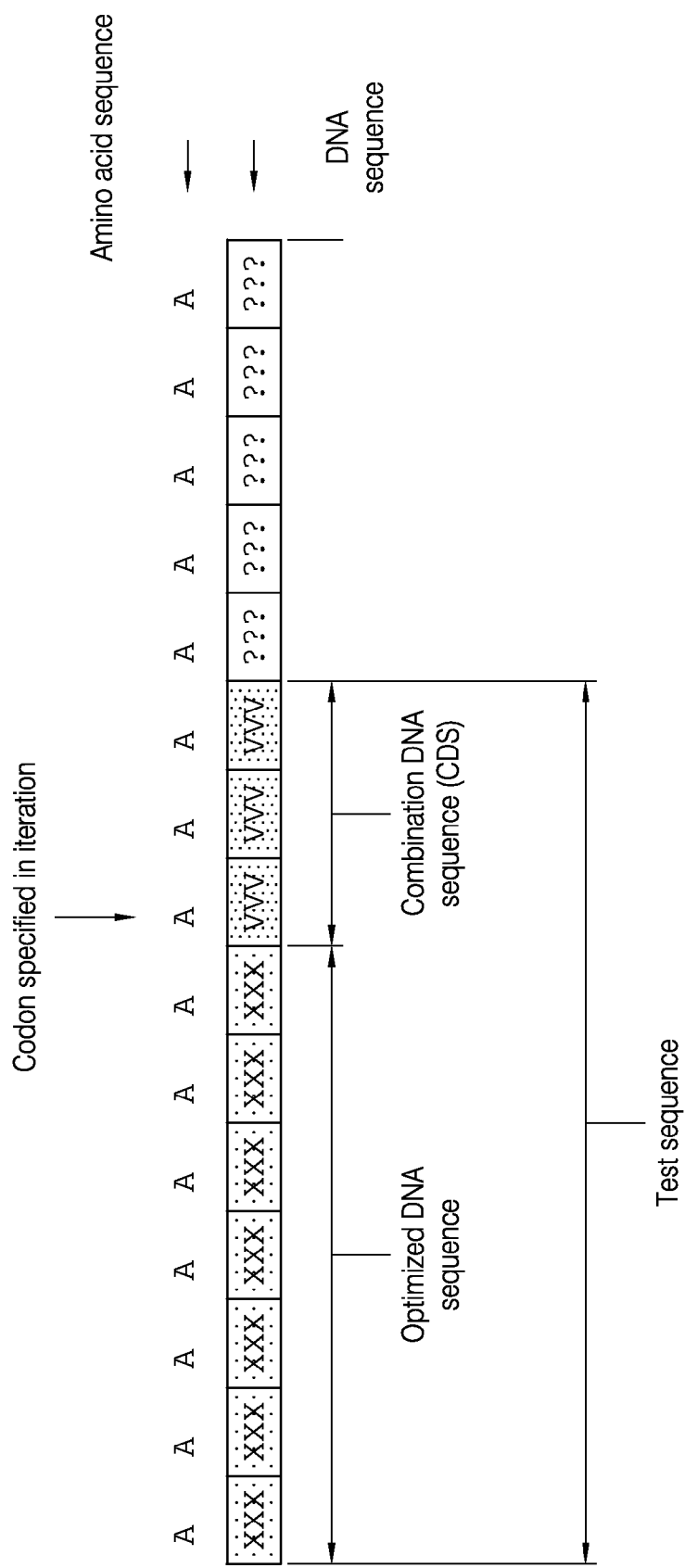
FIG. 2 illustrates the ratio of test sequence, optimized DNA sequence, combination DNA sequence and amino acid sequence for an exemplary embodiment of the invention.

The relationship of the various regions is depicted diagrammatically in FIG. 2. The combination DNA sequence and the region of the previously specified optimized DNA sequence are evident.

The parameter m can be varied within wide limits, the aim being to maximize the number of varied codons for the purpose of the best possible optimization. A worthwhile optimization result can be achieved within an acceptable time with a size of the variation window of from m=5 to m=10 using the computers currently available.

Besides the individual weighting of the criterion weights, it is possible to define both the total weight and the criterion weights by suitable mathematical functions which are modified compared with the simple relations such as difference or proportion, e.g. by segmentally defined functions which define a threshold value, or nonlinear functions. The former is worthwhile for example in assessing repeats or inverse complementary repeats which are to be taken into account only above a certain size. The latter is worthwhile for example in assessing the codon usage or the CG content.

Various examples of weighting criteria which can be used according to the invention are explained below without the invention being restricted to these criteria or the weighting functions described below.

Adaptation of the codon usage of the synthetic gene to the codon usage of the host organism is one of the most important criteria in the optimization. It is necessary to take account in this case of the different degeneracy of the various codons (one-fold to six-fold). Quantities suitable for this purpose are, for example, the RSCU (relative synonymous codon usage) or relative frequencies (relative adaptiveness) which are standardized to the frequency of the codon most used by the organism (the codon used most thus has the codon usage of 1), cf. P. M. Sharp, W. H. Li, Nucleic Acid Research 15 (1987), 1281 to 1295.

To assess a test sequence in one embodiment of the invention, the average codon usage is used on the variation window.

When assessing the GC content, a minimal difference in the average GC content from the predefined desired GC content is necessary. An additional aim should be to keep the variations in the GC content over the course of the sequence small.

To evaluate a test sequence, the average percentage GC content of that region of the test sequence which includes the CDS and bases which are located before the start of the CDS and whose number b is preferably between 20 and 30 bases is ascertained. The criterion weight is ascertained from the absolute value of the difference between the desired GC content and the GC content ascertained for the test sequence, it being possible for this absolute value to enter as argument into a nonlinear function, e.g. into an exponential function.

If the variation window has a width of more than 10 codon positions, variations in the GC content within the CDS may be important. In these cases, as explained above, the GC content for each base position is ascertained on a window which is aligned in a particular way in relation to the base position and may include a particular number of, for example 40, bases, and the absolute values of the difference between the desired GC content and the "local" GC content ascertained for each base position are summed. Division of the sum by the number of individual values ascertained results in the average difference from the desired GC content as criterion weight. In the procedure described above it is possible for the location of the window to be defined so that said base position is located for example at the edge or in the center of the window. An alternative possibility is also to use as criterion the absolute amount of the difference between the actual GC content in the test sequence or on a part region thereof to the desired GC content or the absolute amount of the difference between the average of the abovementioned "local" GC content over the test sequence or a part thereof and the desired GC content as criterion. In a further modification it is also possible to provide for the appropriate criterion weight to be used proportionally to the square of the difference between the actual GC content and the desired GC content, the square of the difference between the GC content averaged over the base positions and the desired GC content or the average of the square of the differences between the local GC content and the desired GC content as criterion. The criterion weight for the GC content has the opposite sign to the criterion weight for the codon usage.

Local recognition sequences or biophysical characteristics play a crucial role in cell biology and molecular biology. Unintended generation of corresponding motifs inside the sequence of the synthesized gene may have unwanted effects. For example, the expression may be greatly reduced or entirely suppressed; an effect toxic for the host organism may also arise. It is therefore desirable in the optimization of the nucleotide sequence to preclude unintended generation of such motifs. In the simplest case, the recognition sequence can be represented by a well-characterized consensus sequence (e.g. restriction enzyme recognition sequence) using appropriate IUPAC base symbols. Carrying out a simple regular expression search within the test sequence results in the number of positions found for calculating the appropriate weight. If a certain number of imperfections (mismatches) is permitted, the number of imperfections in a recognized match must be taken into account when ascertaining the weight function, for example by the local weight for a base position being inversely proportional to the number of bases which are assigned to an IUPAC consensus symbol. However, in many cases the consensus sequence is not sufficiently clear (cf., for example, K. Quandt et al., Nucleic Acid Research 23 (1995), 4878). It is possible in such cases to have recourse to a matrix representation of the motifs or use other recognition methods, e.g. by means of neural networks.

In the preferred embodiment of the invention, a value between 0 and 1 which, in the ideal case, reflects the binding affinity of the (potential) site found or its biological activity or else its reliability of recognition is determined for each motif found. The criterion weight for DNA motifs is calculated by multiplying this value by a suitable weighting factor, and the individual values for each match found are added.

The weight for unwanted motifs is included with the opposite sign to that for the codon usage in the overall quality function.

It is possible in the same way to include in the weighting the presence of certain wanted DNA motifs, e.g. RE cleavage sites, certain enhancer sequences or immunostimulatory or immunosuppressive CpG motifs. The weight for wanted DNA motifs is included with the same sign as the weight for the codon usage in the overall assessment.

Highly repetitive sequence segments may, for example, lead to low genetic stability. The synthesis of repetitive segments is also made distinctly difficult because of the risk of faulty hybridization. According to the preferred embodiment of the invention, therefore, the assessment of a test sequence includes whether it comprises identical or mutually similar sequence segments at various points. The presence of corresponding segments can be established for example with the aid of a variant of a dynamic programming algorithm for generating a local alignment of the mutually similar sequence segments. It is important in this embodiment of the invention that the algorithm used generates a value which is suitable for quantitative description of the degree of matching and/or the length of the mutually similar sequence segments (alignment weight). For further details relating to a possible algorithm, reference is made to the abovementioned textbooks by Gusfield or Waterman and M. S. Waterman, M. Eggert, J. Mol. Biology, (1987) 197, 723 to 728.

To calculate the criterion weight relating to the repetitive elements, the individual weights of all the local alignments where the alignment weight exceeds a certain threshold value are summed. Addition of these individual weights gives the criterion weight which characterizes the repetitiveness of the test sequence.

In a modification of the embodiment described above, only the one region which includes the variation window, and a certain number of further bases, e.g. 20 to 30, at the end of the test sequence is checked for whether a partial segment of the test sequence occurs in identical or similar way in this region of another site of the test sequence. This is depicted diagrammatically in FIG. 3. The full line in the middle represents the complete test sequence. The upper line represents the CDS, while the lower region represents the comparison region of the test sequence, which is checked for matching sequence segments with the remainder of the test sequence. The checking of the test sequences for matching or similar segments of the comparison region (cf. FIG. 3) using the dynamic programming matrix technique is illustrated in FIGS. 4 and 4b. FIG. 4a shows the case where similar or matching sequence segments A and B are present in the comparison region itself. FIG. 4b shows the case where a sequence segment B in the comparison region matches or is similar to a sequence segment A outside the comparison region.

As alternative to the summation of individual weights it is also possible to provide for only the alignment which leads to the highest individual weight or, more generally only the alignments with the m largest individual weights, to be taken into account.

With the weighting described above it is possible to include both similar sequences which are present for example at the start and at the end of the test sequence, and so-called tandem repeats where the similar regions are both located at the end of the sequence.

Inverse complementary repeats can be treated in the same way as simple repeats. The potential formation of secondary structures and the RNA level or cruciform structures at the DNA level can be recognized on the test sequence by the presence of such inverse complementary repeats (inverse repeats). Cruciform structures at the DNA level may impede translation and lead to genetic instability. It is assumed that the formation of secondary structures at the RNA level has adverse effects on translation efficiency. In this connection, inverse repeats of particular importance are those which form hairpin loops or cruciform structures. Faulty hybridizations or hairpin loops may also have adverse effects in the synthesis of the former from oligonucleotides.

The checking for inverse complementary repeats in principle takes place in analogy to the checking for simple repeats. The test sequence or the comparison region of the test sequence is, however, compared with the inverse complementary sequence. In a refinement, the thermodynamic stability can be taken into account in the comparison (alignment), in the simplest case by using a scoring matrix. This involves for example giving higher weight to a CC or GG match, because the base pairing is more stable, than to a TT or AA match. Variable weighting for imperfections (mismatches) is also possible correspondingly. More specific weighting is possible by using nearest neighbor parameters for calculating the thermodynamic stability, although this makes the algorithm more complex. Concerning a possible algorithm, reference is made for example to L. Kaderali, A. Schliep, Bioinformatics 18 (10) 2002, 1340 to 1349.

For all the assessment criteria, the invention can provide for the corresponding weighting function to be position-dependent. For example, a larger weight can be given to the generation of an RE cleavage sequence at a particular site, or a larger weight can be given to secondary structures at the 5' end, because they show stronger inhibition there. It is likewise possible to take account of the codon context, i.e. the preceding or following codon(s). It is additionally possible to provide for certain codons whose use at the domain limits plays a role in cotranslational protein folding to make a contribution to the quality function, which contribution depends on whether this codon is nearer to the domain limit or not. Further criteria which may be included in the quality function are, for example, biophysical properties such as the rigidity or the curvature of the DNA sequence. Depending on the area of use it is also possible to include criteria which are associated with further DNA sequences. For example it is crucial in the area of DNA vaccination that the sequences used for vaccination show no significant similarity to the pathogenic elements of the natural viral genome, in order to reliably preclude unwanted recombination events. In the same way, vectors used for gene therapy purposes ought to show minimal similarity to sequences of the human genome in order firstly to preclude homologous recombination into the human genome and secondly to avoid vital genes being selectively switched off in transcription through RNA interference phenomena (RNAI phenomena). The latter is also of general importance in the production of recombinant cell factories and, in particular, in transgenic organisms.

The various criterion weights for various criteria can according to the invention be included differently in the overall weight function. In this connection the difference which can be maximally achieved through the corresponding criteria in the value of the quality function is important for the test sequence formed. However, a large proportion of certain criterion weights have DNA bases which cannot be changed by different CDS, such as, for example, the nucleotides in front of the CDS, which are also included in the calculation of the average GC content, and the nucleotides which are unaltered within synonymous codons. The individual weighting of a criterion vis-à-vis other criteria can therefore be made dependent on how greatly the quality of the test sequence differs from the target. It may be worthwhile to split up the criterion weights for further processing in mathematical functions for calculating the quality function into a part which is a measure of the portion of a criterion which is variable on use of different CDS, and a part which is a measure of the unaltered portions.

The embodiments of the invention which are described above are explained further below with reference to two specific examples.

EXAMPLE 1

The intention is to ascertain the optimal DNA sequence (SEQ ID NO: 9) pertaining to the (fictional) amino acid sequence AASeq1 (SEQ ID NO:10) from below. A conventional back-translation with optimization for optimal codon usage serves as reference.

```
AASeq1:
ASSeq1:
1    2    3    4    5    6    7    8    9    10   11   12
E__  Q__  F__  I__  I__  K__  N__  M__  F__  I__  I__  K__
GAA  CAG  TTT  ATT  ATT  AAA  AAC  ATG  TTT  ATT  ATT  AAA
GAG  CAA  TTC  ATC  ATC  AAG  AAT       TTC  ATC  ATC  AAG
               ATA  ATA                      ATA  ATA 13   14
N__  A__
AAC  GCG
AAT  GCC
     GCA
     GCT
```

The optimization is based on the following criteria:

the codon usage is to be optimized to the codon usage of *E. Coli* K12.

the GC content is to be as close as possible to 50%.

repetitions are to be excluded as far as possible the Nla III recognition sequence CATG is to be excluded The assessment function used for the codon usage is the following function:

$$CUScore = <CU>$$

where <CU> in this example is the arithmetic mean of the relative adaptiveness over the codon positions of the test sequence.

To represent the codon usage of a codon, for better comparability of the codon quality of different amino acids, the best codon in each case for a particular amino acid is set equal to 100, and the worse codons are rescaled according to their tabulated percentage content. A CUScore of 100 therefore means that only the codons optimal for *E. Coli* K12 are used.

The weight for the percentage GC content is calculated as follows:

$$GCScore = |<GC> - GC_{desire}|^{1.3} \times 0.8$$

Figure 3:
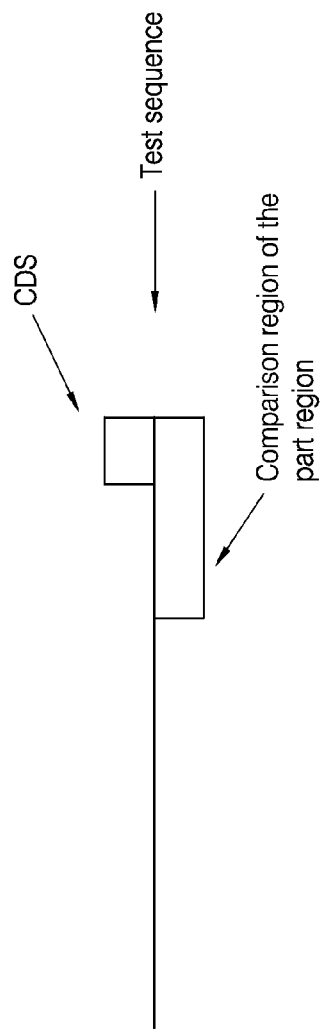
FIG. 3 shows the regions for determining the sequence repeat.
Figure 4A:
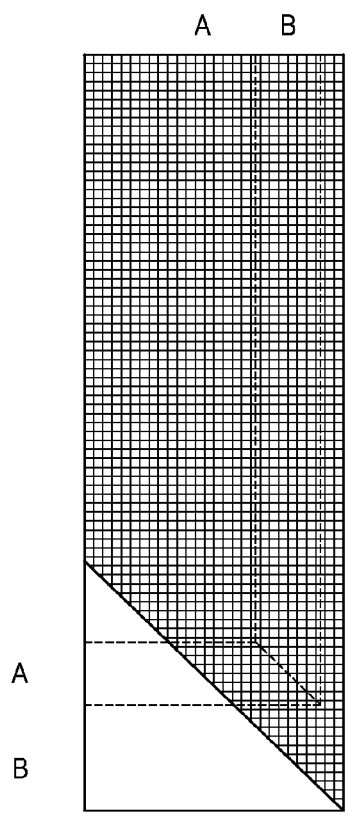
FIGS. 4a and 4b show diagrammatically a scheme for determining sequence repeats.
Figure 4B:
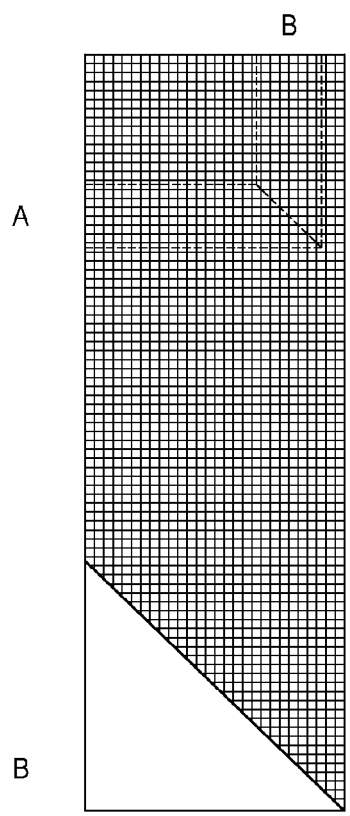

To ascertain the individual weights of the alignments (alignment score), an optimal local alignment of the test sequence with a part region of the test sequence which includes a maximum of the last 36 bases of the complete test sequence is generated with exclusion of the identity alignment (alignment of the complete part region with itself) (cf. FIG. 3, 4a, 4b).

The assessment parameter for a base position used in this case for calculating the dynamic programming matrix are:

Match=1;

Mismatch=−2;

Gap=−2.

The corresponding criterion weight is specified by a power of the optimal alignment score in the examined region of the test sequence:

$$REPScore = (Score_{alignment})^{1.3}$$

A site score of 100 000 is allocated for each CATG sequence found.

The overall quality function TotScore results $$TotScore = CUScore - GCScore - REPScore - SiteScore$$

The CDS length m is 3 codons (9 bases).

An optimization only for optimal codon usage results in the following sequence:

```
1   2   3   4   5   6   7   8   9   10  11  12
E__ Q__ F__ I__ I__ K__ N__ M__ F__ I__ I__ K__
GAA CAG TTT ATT ATT AAA AAC ATG TTT ATT ATT AAA 13  14
N__ A__     SEQ ID NO: 10
AAC GCG     SEQ ID NO: 9
```

It is characterized by the following properties:
highly repetitive, caused by the amino acid sequence F_I_I_K_N (residues 3-7 and 9-13 of SEQ ID NO: 10) which appears twice (the repetitive sequence (bases 7-21 and 25-39 of SEQ ID NO:9) with the highest score (18) is shown):

```
       19           AACATGTTTATTATTAAAAAC
                    **** ***************
        2           AACA-GTTTATTATTAAAAAC
```

GC content: 21.4%
the Nla III recognition sequence CATG is present
average codon usage 100

If the optimization is carried out according to the algorithm of the invention with the abovementioned assessment functions and parameters, the following DNA sequence is obtained:

```
1   2   3   4   5   6   7   8   9   10  11  12
E__ Q__ F__ I__ I__ K__ N__ M__ F__ I__ I__ K__
GAA CAG TTC ATC ATC AAA AAT ATG TTT ATT ATC AAG 13  14
N__ A__     SEQ ID NO: 10
AAC GCG     SEQ ID NO: 9
```

It is characterized by the following properties:
scarcely repetitive (the alignment shown below with the highest contribution has a score of 6)

```
       11    TCATCA
             ||||||
        8    TCATCA
```

GC content: 31.0%
the Nla III recognition sequence CATG has been avoided
average codon usage: 88

In the optimization result according to the invention, the codon optimal in relation to codon usage was not chosen at five amino acid positions. However, the sequence found a represents an optimal balance of the various requirements in terms of codon usage, GC content and ideal sequence properties (avoidance of repetitions).

For the amino acids with the numbers 3, 4, 5, the higher GC content of the codons which are worse in terms of codon usage is the reason for the choice. At position 6, however, on comparison of the codons AAA and AAG, the considerably better codon usage of the AAA codon is dominant, although choice of the AAG codon would lead to a better GC score. On formation of the CDS at base position 13, the codon AAC is preferred for amino acid No. 7 since, with a window size of 3 codons for the CDS, it is not yet evident that this choice will lead to the formation of the CATG DNA motif which is to be avoided (the genetic code is not degenerate for methionine, i.e. there is only one codon for expression of methionine). In the formation of the CDS at base position 16, however, this has been recognized and consequently the codon AAT is chosen. Besides codon usage and GC content, also the avoidance of a repetitive DNA sequence plays in the choice of the codon for amino acids 9 to 13. Because of the identical amino acid sequences of amino acids Nos. 3 to 7 and 9 to 13 a crucial role. For this reason, the codons TTT and ATT are preferred for amino acids 9 and 10, in contrast to previously (Aad. 3,4).

The following table illustrates the individual steps of the algorithm which have led to the optimization result indicated above. It enables the progress of the algorithm to be understood step by step. Moreover, all combination DNA sequences (CDS) formed by the software are listed in detail for each starting position.

The following information is given for each possible CDS:

the test sequence which was formed from each CDS and the previously optimized DNA sequence which is used for evaluating the CDS, the scores which were ascertained for codon usage, GC content, repetitiveness and DNA sites found (CU, GC, Rep, Site)

the repetitive element with the highest alignment score ascertained for the particular test sequence, the total score ascertained.

The CDS are in this case arranged according to decreasing total score, i.e. the first codon of the first CDS shown is attached to the previously optimized DNA sequence. The CDS in the following table correspond to sequences in the attached Sequence Listing, as shown below:

| Starting Amino Acid | CDS | Test Sequence |
|---|---|---|
| 1 E | SEQ ID NO: 11 | bases 1-9 of SEQ ID NO: 9 |
| 2 Q | SEQ ID NO: 12 | bases 1-12 of SEQ ID NO: 9 |
| 3 F | SEQ ID NO: 13 | bases 1-15 of SEQ ID NO: 9 |
| 4 I | SEQ ID NO: 14 | bases 1-18 of SEQ ID NO: 9 |
| 5 I | SEQ ID NO: 15 | bases 1-21 of SEQ ID NO: 9 |
| 6 K | SEQ ID NO: 16 | bases 1-24 of SEQ ID NO: 9 |
| 7 N | SEQ ID NO: 17 | bases 1-27 of SEQ ID NO: 9 |
| 8 M | SEQ ID NO: 18 | bases 1-30 of SEQ ID NO: 9 |
| 9 F | SEQ ID NO: 19 | bases 1-33 of SEQ ID NO: 9 |
| 10 I | SEO ID NO: 20 | bases 1-36 of SEQ ID NO: 9 |
| 11 I | SEQ ID NO: 21 | bases 1-39 of SEQ ID NO: 9 |
| 12 K | SEQ ID NO: 22 | bases 1-42 of SEQ ID NO: 9 |

| CDS test sequence | CU | GC | Site | Rep | Alignment | Total Score |
|---|---|---|---|---|---|---|
| CDS starting position 1 for amino acid 1 E ||||||||
| GAACAGTTC<br>GAACAGTTC | 92 | 5 | 0 | 0.0 | G<br>\|<br>G | 87.0 |
| GAACAGTTT<br>GAACAGTTT | 100 | 19 | 0 | 0.0 | TT<br>\|\|<br>TT | 81.0 |
| GAGCAGTTT<br>GAGCAGTTT | 82 | 5 | 0 | 0.0 | AG<br>\|\|<br>AG | 77.0 |
| GAGCAGTTC<br>GAGCAGTTC | 73 | 5 | 0 | 0.0 | AG<br>\|\|<br>AG | 68.0 |
| GAACAATTC<br>GAACAATTC | 76 | 19 | 0 | 0.0 | AA<br>\|\|<br>AA | 57.0 |
| GAGCAATTC<br>GAGCAATTC | 58 | 5 | 0 | 0.0 | G<br>\|<br>G | 53.0 |
| GAACAATTT<br>GAACAATTT | 85 | 38 | 0 | 0.0 | AA<br>\|\|<br>AA | 47.0 |
| GAGCAATTT<br>GAGCAATTT | 66 | 19 | 0 | 0.0 | TT<br>\|\|<br>TT | 47.0 |
| CDS starting position 4 for amino acid 2 Q ||||||||
| CAGTTCATC<br>GAACAGTTCATC | 86 | 8 | 0 | 0.0 | CA<br>\|\|<br>CA | 78.0 |
| CAGTTTATC<br>GAACAGTTTATC | 94 | 19 | 0 | 0.0 | TT<br>\|\|<br>TT | 75.0 |
| CAGTTCATT<br>GAACAGTTCATT | 92 | 19 | 0 | 0.0 | CA<br>\|\|<br>CA | 73.0 |
| CAGTTTATT<br>GAACAGTTTATT | 100 | 33 | 0 | 0.0 | TT<br>\|\|<br>TT | 67.0 |
| CAATTCATC<br>GAACAATTCATC | 70 | 19 | 0 | 0.0 | AA<br>\|\|<br>AA | 51.0 |
| CAATTTATC<br>GAACAATTTATC | 79 | 33 | 0 | 0.0 | AA<br>\|\|<br>AA | 46.0 |
| CAGTTCATA<br>GAACAGTTCATA | 63 | 19 | 0 | 0.0 | CA<br>\|\|<br>CA | 44.0 |
| CAATTCATT<br>GAACAATTCATT | 76 | 33 | 0 | 0.0 | ATT<br>\|\|\|<br>ATT | 43.0 |
| CAGTTTATA<br>GAACAGTTTATA | 71 | 33 | 0 | 0.0 | TT<br>\|\|<br>TT | 38.0 |

-continued

| CDS test sequence | CU | GC | Site | Rep | Alignment | Total Score |
|---|---|---|---|---|---|---|
| CAATTTATT GAACAATTTATT | 85 | 48 | 0 | 0.0 | ATT ||| ATT | 37.0 |
| CAATTCATA GAACAATTCATA | 48 | 33 | 0 | 0.0 | AA || AA | 15.0 |
| CAATTTATA GAACAATTTATA | 56 | 48 | 0 | 0.0 | AA || AA | 8.0 |
| CDS starting position 7 for amino acid 3 F | | | | | | |
| TTCATCATC GAACAGTTCATCATC | 80 | 10 | 0 | 0.0 | TCATC ||||| TCATC | 70.0 |
| TTTATCATC GAACAGTTTATCATC | 88 | 19 | 0 | 0.0 | ATC ||| ATC | 69.0 |
| TTCATTATC GAACAGTTCATTATC | 86 | 19 | 0 | 0.0 | CA || CA | 67.0 |
| TTCATCATT GAACAGTTCATCATT | 86 | 19 | 0 | 0.0 | TCAT |||| TCAT | 67.0 |
| TTTATTATC GAACAGTTTATTATC | 94 | 30 | 0 | 0.0 | TTAT |||| TTAT | 64.0 |
| TTTATCATT GAACAGTTTATCATT | 94 | 30 | 0 | 0.0 | CA || CA | 64.0 |
| TTCATTATT GAACAGTTCATTATT | 92 | 30 | 0 | 0.0 | ATT ||| ATT | 62.0 |
| TTTATTATT GAACAGTTTATTATT | 100 | 42 | 0 | 0.0 | TTATT ||||| TTATT | 58.0 |
| TTCATCATA GAACAGTTCATCATA | 57 | 19 | 0 | 0.0 | TCAT |||| TCAT | 38.0 |
| TTCATAATC GAACAGTTCATAATC | 57 | 19 | 0 | 0.0 | AA || AA | 38.0 |
| TTTATCATA GAACAGTTTATCATA | 65 | 30 | 0 | 0.0 | CA || CA | 35.0 |
| TTTATAATC GAACAGTTTATAATC | 65 | 30 | 0 | 0.0 | AA || AA | 35.0 |
| TTCATTATA GAACAGTTCATTATA | 63 | 30 | 0 | 0.0 | CA || CA | 33.0 |
| TTCATAATT GAACAGTTCATAATT | 63 | 30 | 0 | 0.0 | AA || AA | 33.0 |
| TTTATTATA GAACAGTTTATTATA | 71 | 42 | 0 | 0.0 | TTAT |||| TTAT | 29.0 |

-continued

| CDS test sequence | CU | GC | Site | Rep | Alignment | Total Score |
|---|---|---|---|---|---|---|
| TTTATAATT<br>GAACAGTTTATAATT | 71 | 42 | 0 | 0.0 | AA<br>\|\|<br>AA | 29.0 |
| TTCATAATA<br>GAACAGTTCATAATA | 34 | 30 | 0 | 0.0 | ATA<br>\|\|\|<br>ATA | 4.0 |
| TTTATAATA<br>GAACAGTTTATAATA | 43 | 42 | 0 | 0.0 | ATA<br>\|\|\|<br>ATA | 1.0 |
| CDS starting position 10 for amino acid 4 I ||||||||
| ATCATCAAA<br>GAACAGTTCATCATCAAA | 88 | 19 | 0 | 0.0 | TCATCA<br>\|\|\|\|\|\|<br>TCATCA | 69.0 |
| ATTATCAAA<br>GAACAGTTCATTATCAAA | 94 | 28 | 0 | 0.0 | TCA<br>\|\|\|<br>TCA | 66.0 |
| ATCATTAAA<br>GAACAGTTCATCATTAAA | 94 | 28 | 0 | 0.0 | TCAT<br>\|\|\|\|<br>TCAT | 66.0 |
| ATTATTAAA<br>GAACAGTTCATTATTAAA | 100 | 38 | 0 | 0.0 | ATTA<br>\|\|\|\|<br>ATTA | 62.0 |
| ATCATCAAG<br>GAACAGTTCATCATCAAG | 65 | 11 | 0 | 0.0 | TCATCA<br>\|\|\|\|\|\|<br>TCATCA | 54.0 |
| ATTATCAAG<br>GAACAGTTCATTATCAAG | 71 | 19 | 0 | 0.0 | TCA<br>\|\|\|<br>TCA | 52.0 |
| ATCATTAAG<br>GAACAGTTCATCATTAAG | 71 | 19 | 0 | 0.0 | TCAT<br>\|\|\|\|<br>TCAT | 52.0 |
| ATTATTAAG<br>GAACAGTTCATTATTAAG | 77 | 28 | 0 | 0.0 | ATTA<br>\|\|\|\|<br>ATTA | 49.0 |
| ATCATAAAA<br>GAACAGTTCATCATAAAA | 65 | 28 | 0 | 0.0 | TCAT<br>\|\|\|\|<br>TCAT | 37.0 |
| ATAATCAAA<br>GAACAGTTCATAATCAAA | 65 | 28 | 0 | 0.0 | TCA<br>\|\|\|<br>TCA | 37.0 |
| ATTATAAAA<br>GAACAGTTCATTATAAAA | 71 | 38 | 0 | 0.0 | AAA<br>\|\|\|<br>AAA | 33.0 |
| ATAATTAAA<br>GAACAGTTCATAATTAAA | 71 | 38 | 0 | 0.0 | TAA<br>\|\|\|<br>TAA | 33.0 |
| ATCATAAAG<br>GAACAGTTCATCATAAAG | 43 | 19 | 0 | 0.0 | TCAT<br>\|\|\|\|<br>TCAT | 24.0 |
| ATAATCAAG<br>GAACAGTTCATAATCAAG | 43 | 19 | 0 | 0.0 | TCA<br>\|\|\|<br>TCA | 24.0 |

-continued

| CDS test sequence | CU | GC | Site | Rep | Alignment | Total Score |
|---|---|---|---|---|---|---|
| ATTATAAAG GAACAGTTCATTATAAAG | 49 | 28 | 0 | 0.0 | AA<br>\|\|<br>AA | 21.0 |
| ATAATTAAG GAACAGTTCATAATTAAG | 49 | 28 | 0 | 0.0 | TAA<br>\|\|\|<br>TAA | 21.0 |
| ATAATAAAA GAACAGTTCATAATAAAA | 43 | 38 | 0 | 0.0 | ATAA<br>\|\|\|\|<br>ATAA | 5.0 |
| ATAATAAAG GAACAGTTCATAATAAAG | 20 | 28 | 0 | 0.0 | ATAA<br>\|\|\|\|<br>ATAA | −8.0 |
| CDS starting position 13 for amino acid 5 I ||||||
| ATCAAAAAC GAACAGTTCATCATCAAAAAC | 94 | 19 | 0 | 0.0 | TCATCA<br>\|\|\|\|\|\|<br>TCATCA | 75.0 |
| ATTAAAAAC GAACAGTTCATCATTAAAAAC | 100 | 27 | 0 | 0.0 | TCAT<br>\|\|\|\|<br>TCAT | 73.0 |
| ATCAAAAAT GAACAGTTCATCATCAAAAAT | 88 | 27 | 0 | 0.0 | TCATCA<br>\|\|\|\|\|\|<br>TCATCA | 61.0 |
| ATTAAAAAT GAACAGTTCATCATTAAAAAT | 94 | 35 | 0 | 0.0 | TCAT<br>\|\|\|\|<br>TCAT | 59.0 |
| ATTAAGAAC GAACAGTTCATCATTAAGAAC | 77 | 19 | 0 | 0.0 | GAAC<br>\|\|\|\|<br>GAAC | 58.0 |
| ATCAAGAAC GAACAGTTCATCATCAAGAAC | 71 | 13 | 0 | 0.0 | TCATCA<br>\|\|\|\|\|\|<br>TCATCA | 58.0 |
| ATCAAGAAT GAACAGTTCATCATCAAGAAT | 65 | 19 | 0 | 0.0 | TCATCA<br>\|\|\|\|\|\|<br>TCATCA | 46.0 |
| ATTAAGAAT GAACAGTTCATCATTAAGAAT | 71 | 27 | 0 | 0.0 | TCAT<br>\|\|\|\|<br>TCAT | 44.0 |
| ATAAAAAAC GAACAGTTCATCATAAAAAAC | 71 | 27 | 0 | 0.0 | TCAT-A-AAAAA<br>\|\|\|\| \| \|\|\|\|\|<br>TCATCATAAAAA | 44.0 |
| ATAAAAAAT GAACAGTTCATCATAAAAAAT | 65 | 35 | 0 | 0.0 | TCAT-A-AAAAA<br>\|\|\|\| \| \|\|\|\|\|<br>TCATCATAAAAA | 30.0 |
| ATAAAGAAC GAACAGTTCATCATAAAGAAC | 49 | 19 | 0 | 0.0 | GAAC<br>\|\|\|\|<br>GAAC | 30.0 |
| ATAAAGAAT GAACAGTTCATCATAAAGAAT | 43 | 27 | 0 | 0.0 | TCAT<br>\|\|\|\|<br>TCAT | 16.0 |
| CDS starting position 16 for amino acid 6 K ||||||
| AAAAATATG GAACAGTTCATCATCAAAAATATG | 94 | 26 | 0 | 0.0 | TCATCA<br>\|\|\|\|\|\|<br>TCATCA | 68.0 |

-continued

| CDS test sequence | CU | GC | Site | Rep | Alignment | Total Score |
|---|---|---|---|---|---|---|
| AAGAATATG GAACAGTTCATCATCAAGAATATG | 71 | 19 | 0 | 0.0 | TCATCA<br>\|\|\|\|\|\|<br>TCATCA | 52.0 |
| AAAAACATG GAACAGTTCATCATCAAAAACATG | 100 | 19 | 200000 | 0.0 | TCATCA<br>\|\|\|\|\|\|<br>TCATCA | 919.0 |
| AAGAACATG GAACAGTTCATCATCAAGAACATG | 77 | 13 | 200000 | 0.0 | TCATCA<br>\|\|\|\|\|\|<br>TCATCA | 936.0 |
| CDS starting position 19 for amino acid 7 N ||||||
| AATATGTTT GAACAGTTCATCATCAAAAATATGTTT | 94 | 35 | 0 | 0.0 | TCATCA<br>\|\|\|\|\|\|<br>TCATCA | 59.0 |
| AATATGTTC GAACAGTTCATCATCAAAAATATGTTC | 86 | 28 | 0 | 0.0 | TCATCA<br>\|\|\|\|\|\|<br>TCATCA | 58.0 |
| AACATGTTT GAACAGTTCATCATCAAAAACATGTTT | 100 | 28 | 200000 | 0.0 | TCATCA<br>\|\|\|\|\|\|<br>TCATCA | 928.0 |
| AACATGTTC GAACAGTTCATCATCAAAAACATGTTC | 92 | 21 | 200000 | 0.0 | AACATGTTC<br>\|\|\|\| \|\|\|\|<br>AACA-GTTC | 929.0 |
| CDS starting position 22 for amino acid 8 M ||||||
| ATGTTTATC GAACAGTTCATCATCAAAAATATGTTTATC | 94 | 35 | 0 | 0.0 | TCATCA<br>\|\|\|\|\|\|<br>TCATCA | 59.0 |
| ATGTTTATT GAACAGTTCATCATCAAAAATATGTTTATT | 100 | 42 | 0 | 0.0 | TCATCA<br>\|\|\|\|\|\|<br>TCATCA | 58.0 |
| ATGTTCATT GAACAGTTCATCATCAAAAATATGTTCATT | 92 | 35 | 0 | 0.0 | GTTCAT<br>\|\|\|\|\|\|<br>GTTCAT | 57.0 |
| ATGTTCATC GAACAGTTCATCATCAAAAATATGTTCATC | 86 | 28 | 0 | 12.5 | GTTCATC<br>\|\|\|\|\|\|\|<br>GTTCATC | 45.0 |
| ATGTTTATA GAACAGTTCATCATCAAAAATATGTTTATA | 71 | 42 | 0 | 0.0 | TCATCA<br>\|\|\|\|\|\|<br>TCATCA | 29.0 |
| ATGTTCATA GAACAGTTCATCATCAAAAATATGTTCATA | 63 | 35 | 0 | 0.0 | GTTCAT<br>\|\|\|\|\|\|<br>GTTCAT | 28.0 |
| CDS starting position 25 for amino acid 9 F ||||||
| TTTATTATC GAACAGTTCATCATCAAAAATATGTTTATTATC | 94 | 42 | 0 | 0.0 | TCATCA<br>\|\|\|\|\|\|<br>TCATCA | 52.0 |
| TTTATCATT GAACAGTTCATCATCAAAAATATGTTTATCATT | 94 | 42 | 0 | 0.0 | TCATCA<br>\|\|\|\|\|\|<br>TCATCA | 52.0 |
| TTCATTATT GAACAGTTCATCATCAAAAATATGTTCATTATT | 92 | 42 | 0 | 0.0 | GTTCAT<br>\|\|\|\|\|\|<br>GTTCAT | 50.0 |
| TTTATCATC GAACAGTTCATCATCAAAAATATGTTTATCATC | 88 | 35 | 0 | 12.5 | GTTTATCATC<br>\|\|\| \|\|\|\|\|\|<br>GTTCATCATC | 40.0 |

-continued

| CDS test sequence | CU | GC | Site | Rep | Alignment | Total Score |
|---|---|---|---|---|---|---|
| TTTATTATT<br>GAACAGTTCATCATCAAAAATATGTTTATTATT | 100 | 49 | 0 | 12.5 | TCATCA--AAAATATCTTTATTATT<br>\|\|\|\|\|\|    \|\|\|\| \|\| \| \| \|\|\|\|\|\|<br>TCATCATCAAAA-ATATGT-TTATT | 38.0 |
| TTCATTATC<br>GAACAGTTCATCATCAAAAATATGTTCATTATC | 86 | 35 | 0 | 12.5 | GTTCATTATC<br>\|\|\|\|\|\|  \|\|\|<br>GTTCATCATC | 38.0 |
| TTCATCATT<br>GAACAGTTCATCATCAAAAATATGTTCATCATT | 86 | 35 | 0 | 17.4 | GTTCATCAT<br>\|\|\|\|\|\|\|\|\|<br>GTTCATCAT | 34.0 |
| TTCATCATC<br>GAACAGTTCATCATCAAAAATATGTTCATCATC | 80 | 28 | 0 | 20.0 | GTTCATCATC<br>\|\|\|\|\|\|\|\|\|\|<br>GTTCATCATC | 32.0 |
| TTTATCATA<br>GAACAGTTCATCATCAAAAATATGTTTATCATA | 65 | 42 | 0 | 0.0 | TCATCA<br>\|\|\|\|\|\|<br>TCATCA | 23.0 |
| TTTATAATC<br>GAACAGTTCATCATCAAAAATATGTTTATAATC | 65 | 42 | 0 | 0.0 | TCATCA<br>\|\|\|\|\|\|<br>TCATCA | 23.0 |
| TTTATTATA<br>GAACAGTTCATCATCAAAAATATGTTTATTATA | 71 | 49 | 0 | 0.0 | TCATCA<br>\|\|\|\|\|\|<br>TCATCA | 22.0 |
| TTATAATT<br>GAACAGTTCATCATCAAAAATATGTTTATAATT | 71 | 49 | 0 | 0.0 | TCATCA<br>\|\|\|\|\|\|<br>TCATCA | 22.0 |
| TTCATAATT<br>GAACAGTTCATCATCAAAAATATGTTCATAATT | 63 | 42 | 0 | 0.0 | GTTCAT<br>\|\|\|\|\|\|<br>GTTCAT | 21.0 |
| TTCATTATA<br>GAACAGTTCATCATCAAAAATATGTTCATTATA | 63 | 42 | 0 | 0.0 | GTTCAT<br>\|\|\|\|\|\|<br>GTTCAT | 21.0 |
| TTCATAATC<br>GAACAGTTCATCATCAAAAATATGTTCATAATC | 57 | 35 | 0 | 12.5 | GTTCATAATC<br>\|\|\|\|\|\|  \|\|\|<br>GTTCATCATC | 9.0 |
| TTCATCATA<br>GAACAGTTCATCATCAAAAATATGTTCATCATA | 57 | 35 | 0 | 17.4 | GTTCATCAT<br>\|\|\|\|\|\|\|\|\|<br>GTTCATCAT | 5.0 |
| TTTATAATA<br>GAACAGTTCATCATCAAAAATATGTTTATAATA | 43 | 49 | 0 | 0.0 | TCATCA<br>\|\|\|\|\|\|<br>TCATCA | −6.0 |
| TTCATAATA<br>GAACAGTTCATCATCAAAAATATGTTCATAATA | 34 | 42 | 0 | 0.0 | GTTCAT<br>\|\|\|\|\|\|<br>GTTCAT | −8.0 |
| CDS starting position 28 for amino acid 10 I | | | | | | |
| ATTATCAAA<br>GAACAGTTCATCATCAAAAATATGTTATTATCAAA | 94 | 49 | 0 | 12.5 | GTTTATTATCAAA<br>\|\|\| \|\| \|\|\|\|\|\|<br>GTTCATCATCAAA | 32.0 |
| ATCATTAAA<br>GAACAGTTCATCATCAAAAATATGTTATCATTAAA | 94 | 49 | 0 | 12.5 | GTTTATCATTAAA<br>\|\|\| \|\|\|\|\|\| \|\|\|<br>GTTCATCATCAAA | 32.0 |
| ATTATCAAG<br>GAACAGTTCATCATCAAAAATATGTTATTATCAAG | 71 | 42 | 0 | 0.0 | TCATCA<br>\|\|\|\|\|\|<br>TCATCA | 29.0 |
| ATCATTAAG<br>GAACAGTTCATCATCAAAAATATGTTATCATTAAG | 71 | 42 | 0 | 0.0 | TCATCA<br>\|\|\|\|\|\|<br>TCATCA | 29.0 |

-continued

| CDS test sequence | CU | GC | Site | Rep | Alignment | Total Score |
|---|---|---|---|---|---|---|
| ATTATTAAA GAACAGTTCATCATCAAAAATATGTTTATTATTAAA | 100 | 57 | 0 | 14.9 | TCATCA--AAAATATGTTTATTATTA<br>||||||  |||| || | | ||||||<br>TCATCATCAAAA-ATATGT-TTATTA | 28.0 |
| ATCATCAAA GAACAGTTCATCATCAAAAATATGTTTATCATCAAA | 88 | 42 | 0 | 20.0 | GTTTATCATCAAA<br>||| ||||||||||<br>GTTCATCATCAAA | 26.0 |
| ATTATAAAA GAACAGTTCATCATCAAAAATATGTTTATTATAAAA | 71 | 57 | 0 | 0.0 | TCATCA<br>||||||<br>TCATCA | 14.0 |
| ATAATTAAA GAACAGTTCATCATCAAAAATATGTTTATAATTAAA | 71 | 57 | 0 | 0.0 | TCATCA<br>||||||<br>TCATCA | 14.0 |
| ATTATTAAG GAACAGTTCATCATCAAAAATATGTTTATTATTAAG | 77 | 49 | 0 | 14.9 | TCATCA--AAAATATGTTTATTATTA<br>||||||  |||| || | | ||||||<br>TCATCATCAAAA-ATATGT-TTATTA | 13.0 |
| ATCATCAAG GAACAGTTCATCATCAAAAATATGTTTATCATCAAG | 65 | 35 | 0 | 17.4 | GTTTATCATCAA<br>||| |||||||||<br>GTTCATCATCAA | 13.0 |
| ATAATCAAA GAACAGTTCATCATCAAAAATATGTTTATAATCAAA | 65 | 49 | 0 | 12.5 | GTTTATAATCAAA<br>||| || ||||||<br>GTTCATCATCAAA | 3.0 |
| ATCATAAAA GAACAGTTCATCATCAAAAATATGTTTATCATAAAA | 65 | 49 | 0 | 14.9 | GTTTATCAT-AAAA<br>||| ||||| ||||<br>GTTCATCATCAAAA | 1.0 |
| ATAATCAAG GAACAGTTCATCATCAAAAATATGTTTATAATCAAG | 43 | 42 | 0 | 0.0 | TCATCA<br>||||||<br>TCATCA | 1.0 |
| ATTATAAAG GAACAGTTCATCATCAAAAATATGTTTATTATAAAG | 49 | 49 | 0 | 0.0 | TCATCA<br>||||||<br>TCATCA | 0.0 |
| ATAATTAAG GAACAGTTCATCATCAAAAATATGTTTATAATTAAC | 49 | 49 | 0 | 0.0 | TCATCA<br>||||||<br>TCATCA | 0.0 |
| ATCATAAG GAACAGTTCATCATCAAAAATATGTTTATCATAAAG | 43 | 42 | 0 | 12.5 | GTTTATCAT-AAA<br>||| ||||| |||<br>GTTCATCATCAAA | −12.0 |
| ATAATAAAA GAACAGTTCATCATCAAAAATATGTTTATAATAAAA | 43 | 57 | 0 | 0.0 | TCATCA<br>||||||<br>TCATCA | −14.0 |
| ATAATAAAG GAACAGTTCATCATCAAAAATATGTTTATAATAAAG | 20 | 49 | 0 | 0.0 | TCATCA<br>||||||<br>TCATCA | −29.0 |
| CDS starting position 31 for amino acid 11 I | | | | | | |
| ATCAAGAAC GAACAGTTCATCATCAAAAATATGTTTATTATCAAGAAC | 71 | 42 | 0 | 0.0 | TCATCA<br>||||||<br>TCATCA | 29.0 |
| ATTAAAAAC GAACAGTTCATCATCAAAAATATGTTTATTATTAAAAAC | 100 | 57 | 0 | 14.9 | TCATCA--AAAATATGTTTATTATTA<br>||||||  |||| || | | ||||||<br>TCATCATCAAAA-ATATGT-TTATTA | 28.0 |
| ATCAAAAAC GAACAGTTCATCATCAAAAATATGTTTATTATCAAAAAC | 94 | 49 | 0 | 17.4 | GTTTATTATCAAAAA<br>||| || |||||||||<br>GTTCATCATCAAAAA | 28.0 |

-continued

| CDS test sequence | CU | GC | Site | Rep | Alignment | Total Score |
|---|---|---|---|---|---|---|
| ATTAAAAAT<br>GAACAGTTCATCATCAAAAATATGTTTATTATTAAAAAT | 94 | 64 | 0 | 14.9 | TCATCA--AAAATATGTTTATTATTA<br>\|\|\|\|\|\|   \|\|\|\| \|\| \| \|  \|\|\|\|\|\|<br>TCATCATCAAAA-ATATGT-TTATTA | 15.0 |
| ATTAAGAAC<br>GAACAGTTCATCATCAAAAATATGTTTATTATTAAGAAC | 77 | 49 | 0 | 14.9 | TCATCA--AAAATATGTTTATTATTA<br>\|\|\|\|\|\|   \|\|\|\| \|\| \| \|  \|\|\|\|\|\|<br>TCATCATCAAAA-ATATGT-TTATTA | 13.0 |
| ATCAAAAAT<br>GAACAGTTCATCATCAAAAATATGTTTATTATCAAAAAT | 88 | 57 | 0 | 20.0 | GTTTATTATCAAAAAT<br>\|\|\| \|\| \|\|\|\|\|\|\|\|<br>GTTCATCATCAAAAAT | 11.0 |
| ATCAAGAAT<br>GAACAGTTCATCATCAAAAATATGTTTATTATCAAGAAT | 65 | 49 | 0 | 12.5 | GTTTATTATCAAGAAT<br>\|\|\| \|\| \|\|\|\|\| \|\|\|<br>GTTCATCATCAAAAAT | 3.0 |
| ATAAAGAAC<br>GAACAGTTCATCATCAAAAATATGTTTATTATAAAGAAC | 49 | 49 | 0 | 0.0 | TCATCA<br>\|\|\|\|\|\|<br>TCATCA | 0.0 |
| ATTAAGAAT<br>GAACAGTTCATCATCAAAAATATGTTTATTATTAAGAAT | 71 | 57 | 0 | 14.9 | TCATCA--AAAATATGTTTATTATTA<br>\|\|\|\|\|\|   \|\|\|\| \|\| \| \|  \|\|\|\|\|\|<br>TCATCATCAAAA-ATATGT-TTATTA | −1.0 |
| ATAAAAAAC<br>GAACAGTTCATCATCAAAAATATGTTTATTATAAAAAAC | 71 | 57 | 0 | 14.9 | TCATCA--AAAATATGTTTATTA-TA-AAAAA<br>\|\|\|\|\|\|   \|\|\|\| \|\| \| \| \|\|\| \|\| \|\|\|\|\|<br>TCATCATCAAAA-ATATGT-TTATTATAAAAA | −1.0 |
| ATAAAAAAT<br>GAACAGTTCATCATCAAAAATATGTTTATTATAAAAAAT | 65 | 64 | 0 | 14.9 | TCATCA--AAAATATGTTTATTA-TA-AAAAA<br>\|\|\|\|\|\|   \|\|\|\| \|\| \| \| \|\|\| \|\| \|\|\|\|\|<br>TCATCATCAAAA-ATATGT-TTATTATAAAAA | −14.0 |
| ATAAAGAAT<br>GAACAGTTCATCATCAAAAATATGTTTATTATAAAGAAT | 43 | 57 | 0 | 0.0 | TCATCA<br>\|\|\|\|\|\|<br>TCATCA | −14.0 |
| CDS starting position 34 for amino acid 12 K | | | | | | |
| AAGAACGCG<br>GAACAGTTCATCATCAAAAATATGTTTATTATCAAGAA-CGCG | 77 | 28 | 0 | 0.0 | TCATCA<br>\|\|\|\|\|\|<br>TCATCA | 49.0 |
| AAAAACGCG<br>GAACAGTTCATCATCAAAAATATGTTTATTATCAAAAA-CGCG | 100 | 35 | 0 | 17.4 | GTTTATTATCAAAAA<br>\|\|\| \|\| \|\|\|\|\|\|\|<br>GTTCATCATCAAAAA | 48.0 |
| AAGAACGCC<br>GAACAGTTCATCATCAAAAATATGTTTATTATCAAGAA-CGCC | 69 | 28 | 0 | 0.0 | TCATCA<br>\|\|\|\|\|\|<br>TCATCA | 41.0 |
| AAAAACGCC<br>GAACAGTTCATCATCAAAAATATGTTTATTATCAAAAA-CGCC | 92 | 35 | 0 | 17.4 | GTTTATTATCAAAAA<br>\|\|\| \|\| \|\|\|\|\|\|\|<br>GTTCATCATCAAAAA | 40.0 |
| AAAAATGCG<br>GAACAGTTCATCATCAAAAATATGTTTATTATCAAAAA-TGCG | 94 | 42 | 0 | 20.0 | GTTTATTATCAAAAAT<br>\|\|\| \|\| \|\|\|\|\|\|\|\|<br>GTTCATCATCAAAAAT | 32.0 |
| AAGAACGCA<br>GAACAGTTCATCATCAAAAATATGTTTATTATCAAGAA-CGCA | 63 | 35 | 0 | 0.0 | TCATCA<br>\|\|\|\|\|\|<br>TCATCA | 28.0 |
| AAAAACGCA<br>GAACAGTTCATCATCAAAAATATGTTTATTATCAAAAA-CGCA | 86 | 42 | 0 | 17.4 | GTTTATTATCAAAAA<br>\|\|\| \|\| \|\|\|\|\|\|\|<br>GTTCATCATCAAAAA | 27.0 |
| AAAAATGCC<br>GAACAGTTCATCATCAAAAATATGTTTATTATCAAAAA-TGCC | 86 | 42 | 0 | 20.0 | GTTTATTATCAAAAAT<br>\|\|\| \|\| \|\|\|\|\|\|\|\|<br>GTTCATCATCAAAAAT | 24.0 |
| AAGAACGCT<br>GAACAGTTCATCATCAAAAATATGTTTATTATCAAGAA-CGCT | 59 | 35 | 0 | 0.0 | TCATCA<br>\|\|\|\|\|\|<br>TCATCA | 24.0 |

-continued

| CDS test sequence | CU | GC | Site | Rep | Alignment | Total Score |
|---|---|---|---|---|---|---|
| AAGAATGCG GAACAGTTCATCATCAAAAATATGTTTATTATCAAGAA- TGCG | 71 | 35 | 0 | 12.5 | GTTTATTATCAAGAAT<br>||| || ||||| |||<br>GTTCATCATCAAAAAT | 23.0 |
| AAAAACGCT GAACAGTTCATCATCAAAAATATGTTTATTATCAAAAA- CGCT | 81 | 42 | 0 | 17.4 | GTTTATTATCAAAAA<br>||| || ||||||||<br>GTTCATCATCAAAAA | 22.0 |
| AAGAATGCC GAACAGTTCATCATCAAAAATATGTTTATTATCAAGAA- TGCC | 63 | 35 | 0 | 12.5 | GTTTATTATCAAGAAT<br>||| || ||||| |||<br>GTTCATCATCAAAAAT | 15.0 |
| AAAAATGCA GAACAGTTCATCATCAAAAATATGTTTATTATCAAAAA- TGCA | 80 | 49 | 0 | 20.0 | GTTTATTATCAAAAAT<br>||| || |||||||||<br>GTTCATCATCAAAAAT | 11.0 |
| AAAAATGCT GAACAGTTCATCATCAAAAATATGTTTATTATCAAAAA- TGCT | 75 | 49 | 0 | 20.0 | GTTTATTATCAAAAAT<br>||| || |||||||||<br>GTTCATCATCAAAAAT | 6.0 |
| AAGAATGCA GAACAGTTCATCATCAAAAATATGTTTATTATCAAGAA- TGCA | 57 | 42 | 0 | 12.5 | GTTTATTATCAAGAAT<br>||| || ||||| |||<br>GTTCATCATCAAAAAT | 2.0 |
| AAGAATGCT GAACAGTTCATCATCAAAAATATGTTTATTATCAAGAA- TGCT | 53 | 42 | 0 | 12.5 | GTTTATTATCAAGAAT<br>||| || ||||| |||<br>GTTCATCATCAAAAAT | -2.0 |

EXAMPLE 2

This example considers the optimization of GFP for expression in *E. Coli*.
Origin of the amino acid sequence (SEQ ID NO: 23):

```
DEFINITION   Aequorea victoria green-fluorescent
             protein mRNA, complete cds.
ACCESSION    M62654
```

MSKGEELFTGVVPILVELDGDVNGHKFSVSGEGEGDATYGKLTLKFICTT

GKLPVPWPTLVTTFSYGVQCFSRYPDHMKQHDFFKSAMPEGYVQERTIFY

KDDGNYKSRAEVKFEGDTLVNRIELKGIDFKEDGNILGHKMEYNYNSHNV

YIMADKQKNGIKVNFKIRHNIEDGSVQLADHYQQNTPIGDGPVLLPDNHY

LSTQSALSKDPNEKRDHMILLEFVTAAGITHGMDELYK

Figure 5A:
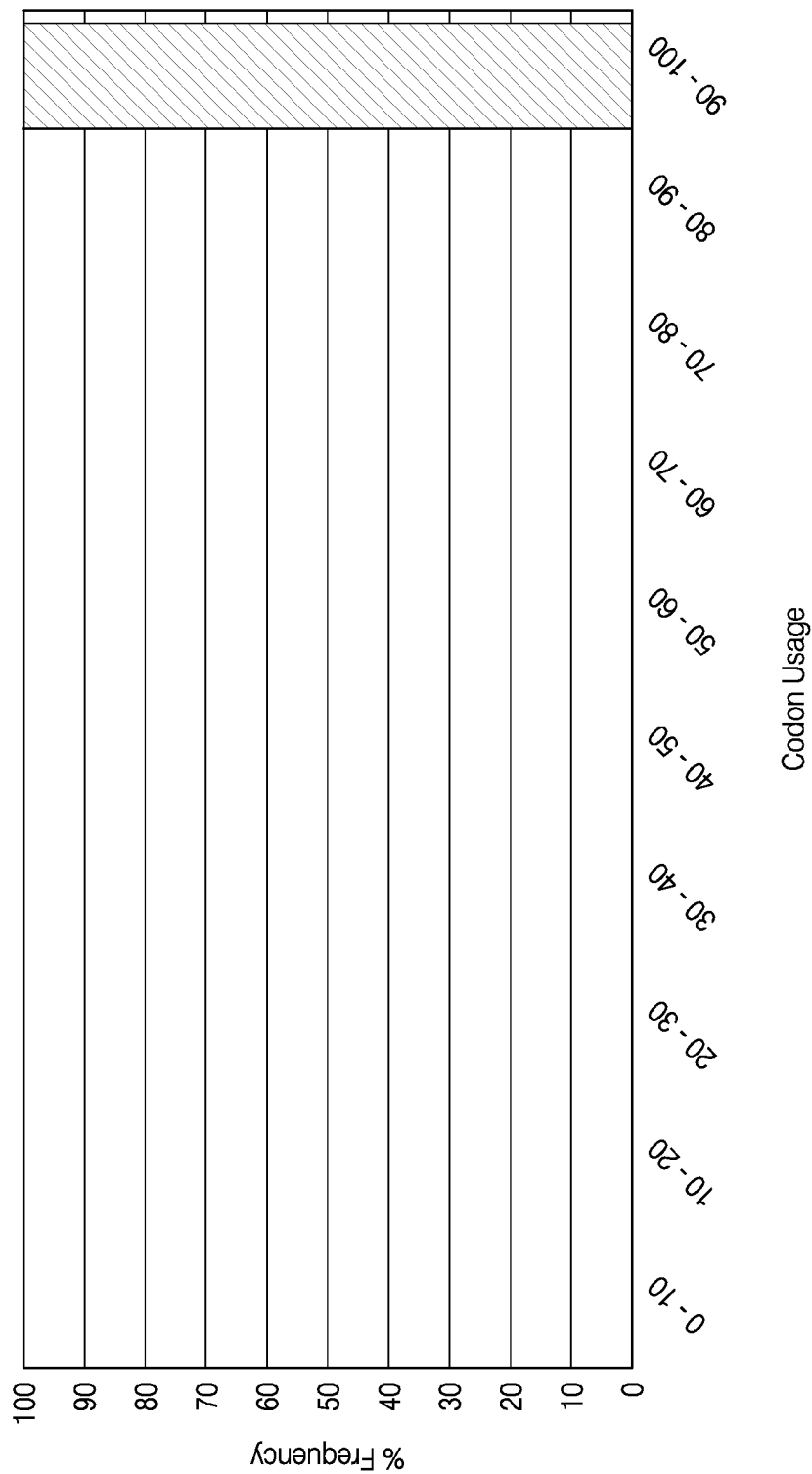
FIG. 5a shows the codon usage on exclusive optimization for codon usage.
Figure 5B:
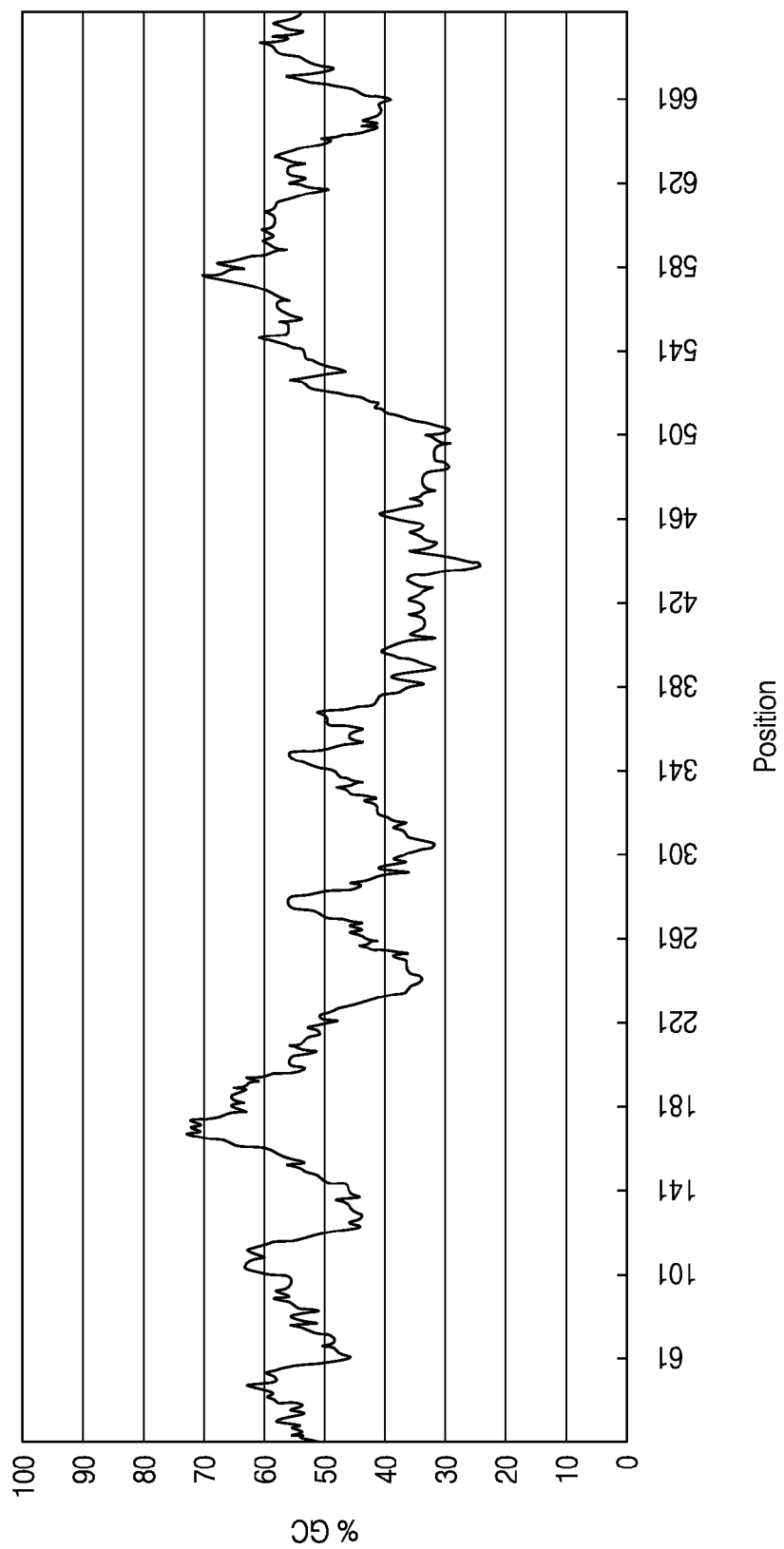
FIG. 5b shows the GC content on exclusive optimization for codon usage.

Codon usage table used: *Escherichia coli* K12
Origin: online codon usage database
The meanings below are:
<CU>: average renormalized codon usage of the CDS (15 bases long)
<GC>: average percentage GC content of the last 35 bases of the test sequence
$GC_{desire}$: desired GC content
The size of the window on which the GC content was calculated for the graphical representation in FIG. 5*b* to 8*b* was 40 bases FIGS. 5*a* and 5*b* show the results for the quality function:

Score=<CU>

Figure 6A:
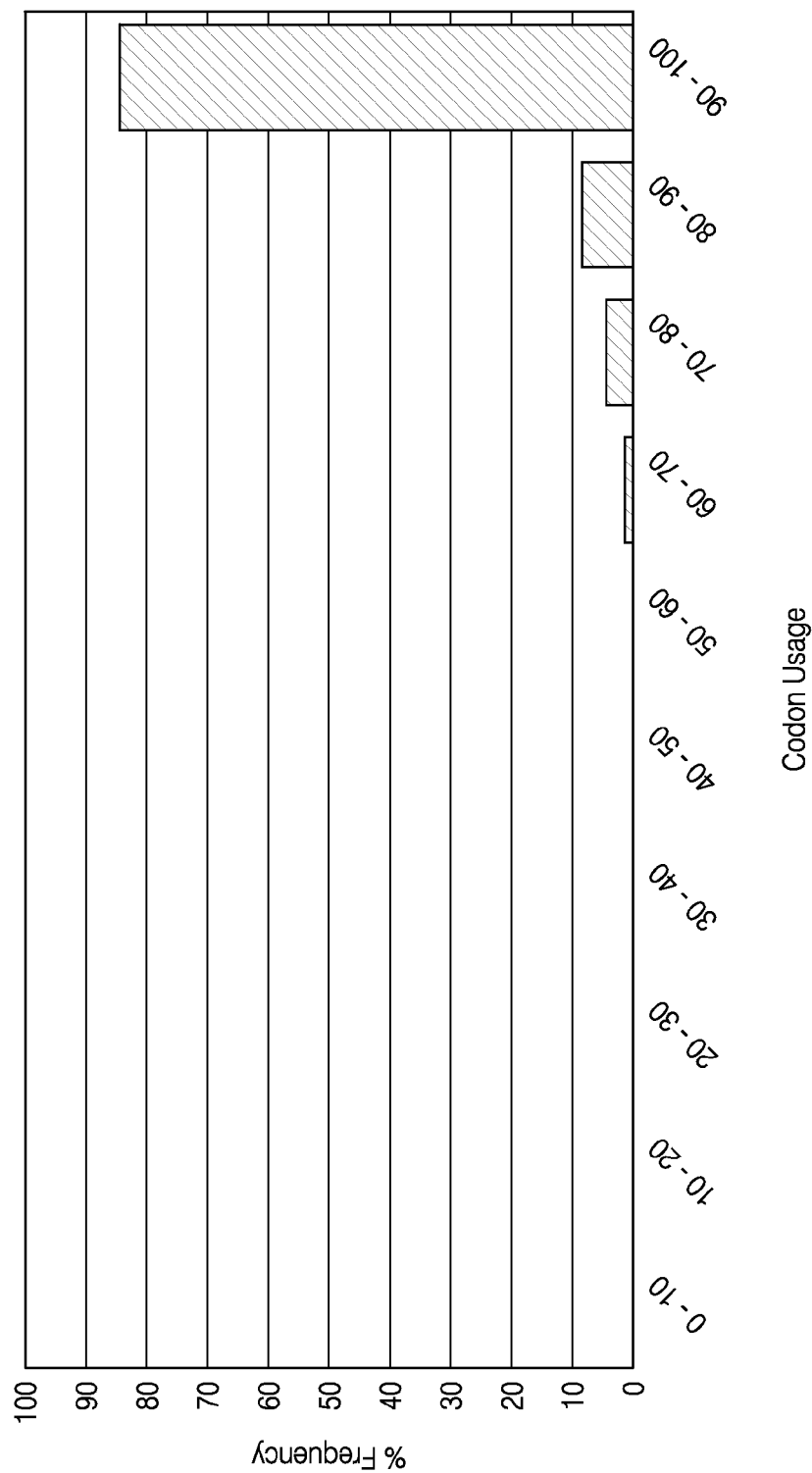
FIG. 6a shows the codon usage on use of a first quality function.
Figure 6B:
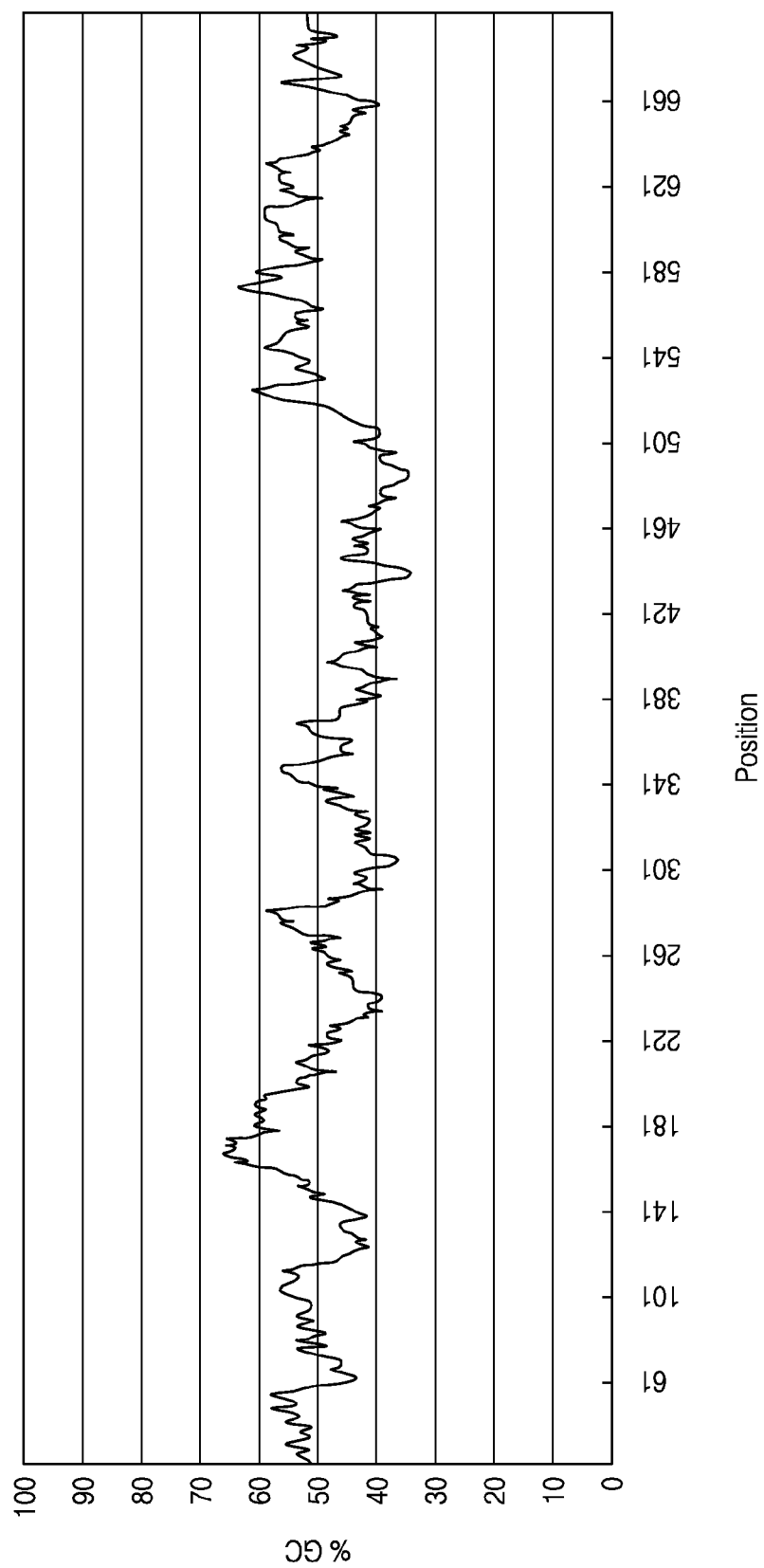
FIG. 6b shows the GC content on use of a first quality function.

FIGS. 6*a* and 6*b* show the results for the quality function

Score=<CU>-|<GC>-$GC_{desire}$|$^{1.3}$×0.8

Figure 7A:
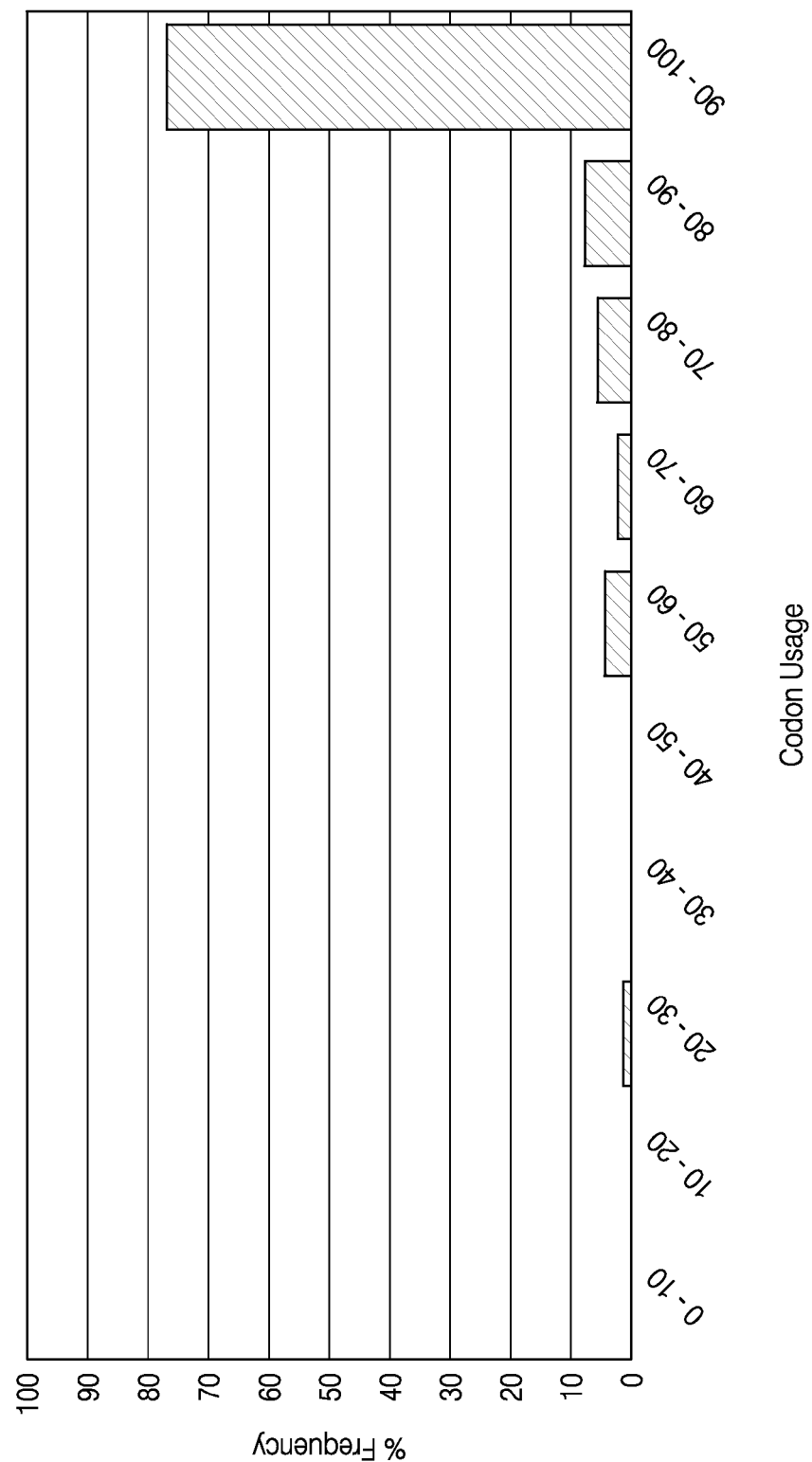
FIG. 7a shows the codon usage on use of a second quality function.
Figure 7B:
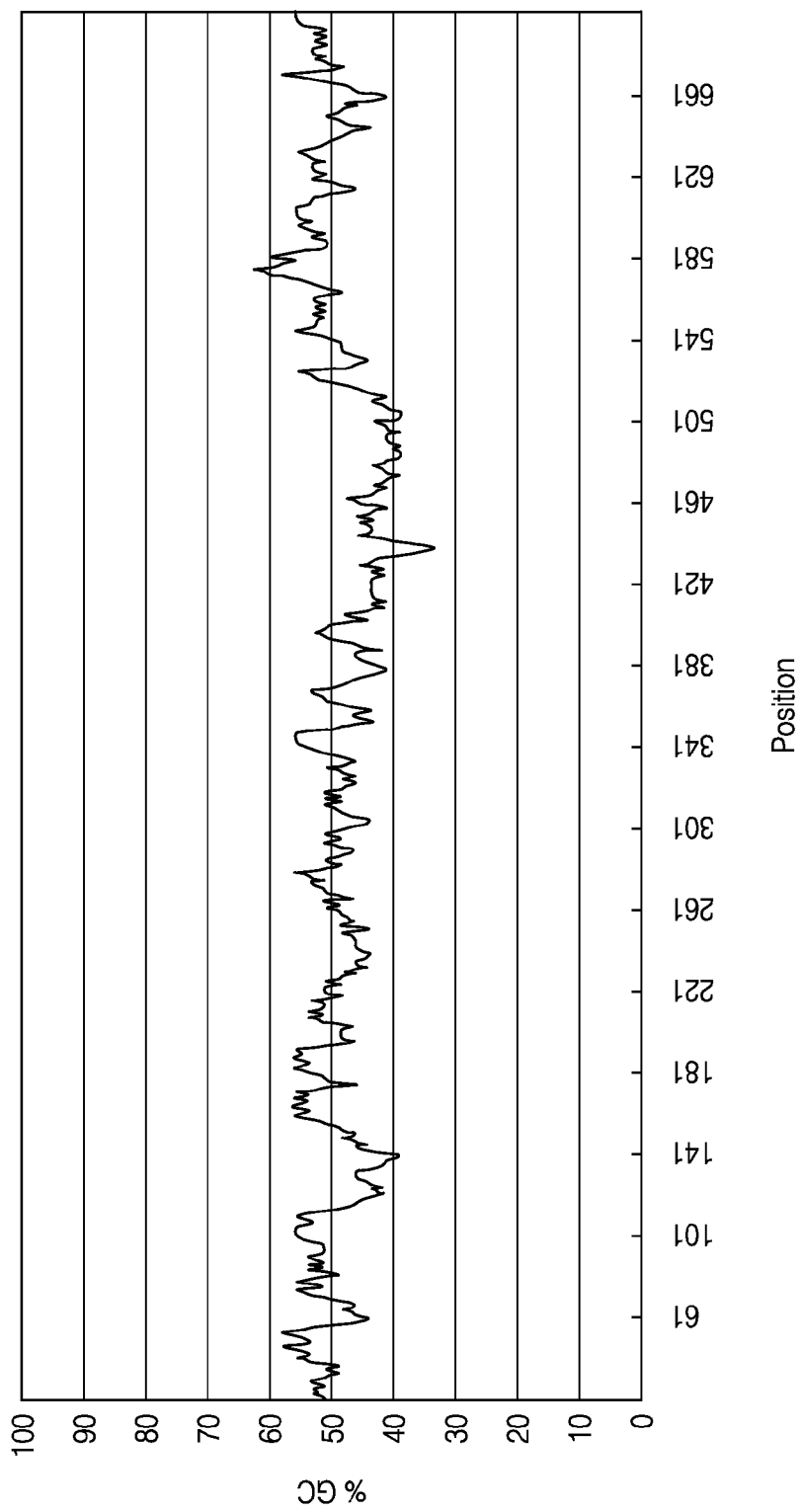
FIG. 7b shows the GC content on use of a second quality function.

FIGS. 7*a* and 7*b* show the results for the quality function

Score=<CU>-|<GC>-$GC_{desire}$|$^{1.3}$×1.5

Figure 8A:
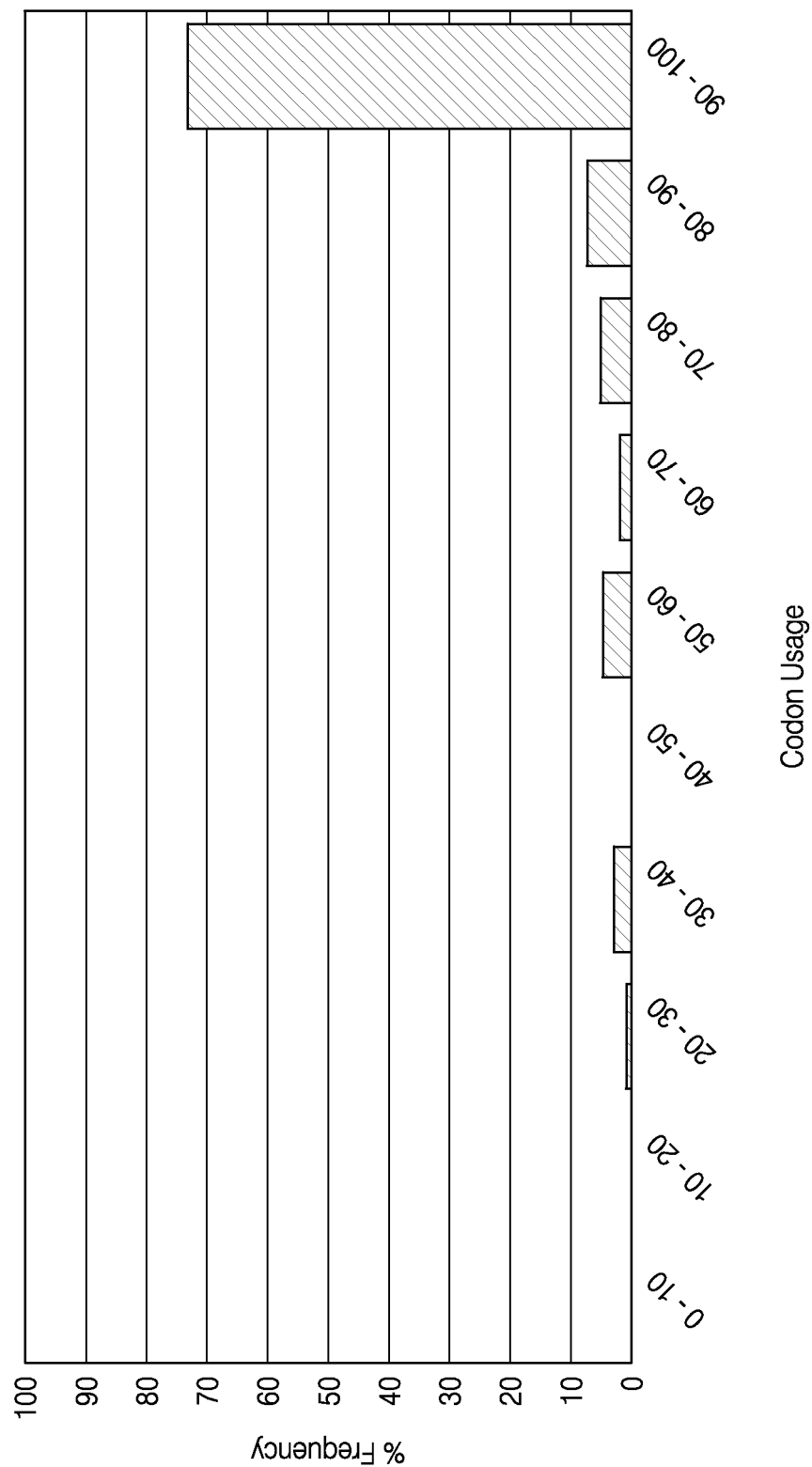
FIG. 8a shows the codon usage on use of a third quality function.
Figure 8B:
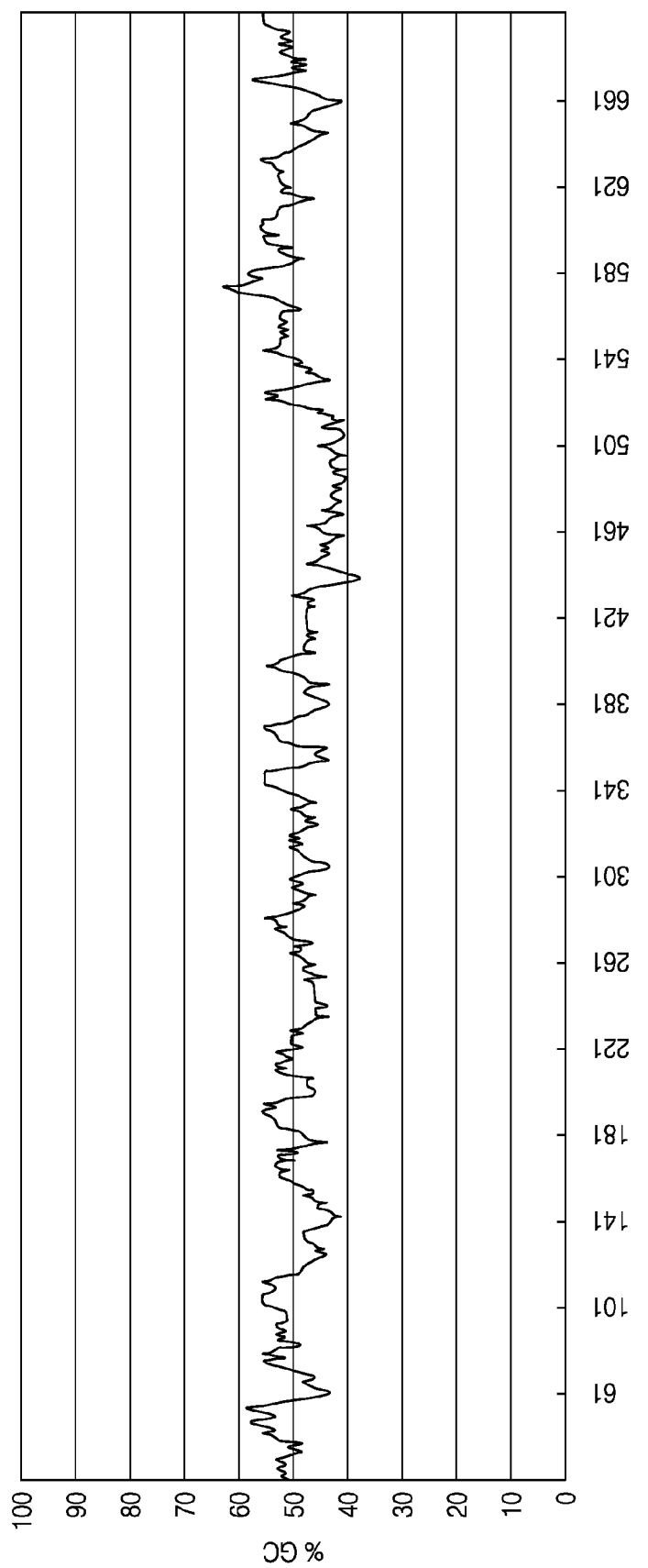
FIG. 8b shows the GC content on use of a third quality function.

FIGS. 8*a* and 8*b* show the results for the quality function

Score=<CU>-|<GC>-$GC_{desire}$|$^{1.3}$×5

FIGS. 5 to 8 illustrate the influence of the different weighting of two optimization criteria on the optimization result. The aim is to smooth the GC content distribution over the sequence and approach the value of 50%. In the case shown in FIGS. 5*a* and 5*b*, optimization was only for optimal codon usage, resulting in a very heterogeneous GC distribution which in some cases differed greatly from the target content. In the case of FIGS. 6*a* and 6*b* there is an ideal conjunction of a smoothing of the GC content to a value around 50% with a good to very good codon usage. The cases of FIGS. 7*a* and 7*b*, and 8*a* and 8*b*, finally illustrate that although a further GC content optimization is possible, it is necessarily at the expense of a poor codon usage in places.

EXAMPLE 3

The efficiency of the method of the invention is illustrated by the following exemplary embodiment in which expression constructs with adapted and RNA- and codon-optimized reading frames were prepared, and in which the respective expression of the protein was quantified.

Selected cytokine genes and chemokine genes from various organisms (human: IL15, GM-CSF and mouse: GM-CSF, MIP1alpha) were cloned into the plasmid pcDNA3.1(+) (In-vitrogen) to prepare expression plasmids. The reading frames of the corresponding genes were optimized using a codon choice like that preferentially found in human and murine cells, respectively, and using the optimization method described herein for maximal expression in the relevant organism. The corresponding genes were artificially assembled after the amino acid sequence of the genes was initially translated into a nucleotide sequence like that calculated by the described method taking account of various parameters.

The optimization of the cytokine genes was based on the following parameters:

the following quality function was used to assess the test sequence:

TotScore=CUScore-GCScore-REPScore-SEKscore-SiteScore

The CDS length was 5 codons.
The individual scores are in this case defined as follows:

CUScore=<CU>  a)

where <CU> represents the arithmetic mean of the relative adaptiveness values of the CDS codons, multiplied by 100, i.e. to represent the codon usage of a codon, for better comparability of the codon quality of different amino acids the codon which is best in each case for a particular amino acid is set equal to 100, and the worst codons are rescaled according to their tabulated percentage content. A CUScore of 100 therefore means that only codons optimal for the expression system are used. In the cytokine genes to be optimized, the CUScore was calculated on the basis of the codon frequencies in humans (*Homo sapiens*) which are listed in the table below. Only codons whose relative adaptiveness is greater than 0.6 are used in the optimizations.

| AmAcid | Codon | Frequency |
|---|---|---|
| Ala | GCG | 0.10 |
|  | GCA | 0.23 |
|  | GCT | 0.26 |
|  | GCC | 0.40 |
| Arg | AGG | 0.20 |
|  | AGA | 0.20 |
|  | CGG | 0.20 |
|  | CGA | 0.11 |
|  | CGT | 0.06 |
|  | CGC | 0.19 |
| Asn | AAT | 0.45 |
|  | AAC | 0.55 |
| Asp | GAT | 0.46 |
|  | GAC | 0.54 |
| Cys | TGT | 0.45 |
|  | TGC | 0.55 |
| End | TGA | 0.61 |
|  | TAG | 0.17 |
|  | TAA | 0.21 |
| Gln | CAG | 0.73 |
|  | CAA | 0.27 |
| Glu | GAG | 0.58 |
|  | GAA | 0.42 |
| Gly | GGG | 0.25 |
|  | GGA | 0.25 |
|  | GGT | 0.16 |
|  | GCC | 0.34 |
| His | CAT | 0.41 |
|  | CAC | 0.59 |
| Ile | ATA | 0.18 |
|  | ATT | 0.35 |
|  | ATC | 0.47 |
| Leu | TTG | 0.12 |
|  | TTA | 0.08 |
|  | CTG | 0.38 |
|  | CTA | 0.09 |
|  | CTT | 0.13 |
|  | CTC | 0.20 |
| Lys | AAG | 0.56 |
|  | AAA | 0.44 |
| Met | ATG | 1.00 |
| Phe | TTT | 0.45 |
|  | TTC | 0.55 |
| Pro | CCG | 0.11 |
|  | CCA | 0.27 |
|  | CCT | 0.28 |
|  | CCC | 0.34 |
| Ser | AGT | 0.15 |
|  | AGC | 0.24 |
|  | TCG | 0.05 |
|  | TCA | 0.15 |
|  | TCT | 0.18 |
|  | TCC | 0.22 |
| Thr | ACG | 0.11 |
|  | ACA | 0.29 |
|  | ACT | 0.24 |
|  | ACC | 0.37 |
| Trp | TGG | 1.00 |
| Tyr | TAT | 0.44 |
|  | TAC | 0.56 |
| Val | GTG | 0.45 |
|  | GTA | 0.12 |
|  | GTT | 0.18 |
|  | GTC | 0.24 |

Source: GENBANK™ release 138.0 [Oct. 15, 2003] codon usage database

GCScore=|<GC>-GC$_{desire}$|×2  b)

with <GC>: average percentage GC content of the last 35 bases of the test sequence
GC$_{desire}$: desired percentage GC content of 60%

REPScore=(Score$_{alignment,max}$)  c)

To ascertain the individual weights of the alignments (alignment score), a local alignment of a terminal part region of the test sequence which includes a maximum of the last 35 bases of the complete test sequence is carried out with the region located in front in the test sequence.

Assessment parameters used in this case for a base position are:
Match=10;
Mismatch=−30;
Gap=−30.

The corresponding criterion weight REPScore is defined as the highest alignment score Score$_{alignment,maxt}$ reached in the checked region of the test sequence. If the value of Score$_{alignment,max}$) is <100, then REPScore is set equal to 0.

SEKScore=(Score$_{InvAligne\,nl\,max}$)  d)

The criterion weight SEKScore weights inverse alignments in the sequence produced. To ascertain the individual weight of an alignment (Score$_{InvAlignment,max}$), a local alignment of the inverse complementary of the test sequence is carried out with the part region of the test sequence which includes a maximum of the last 35 bases of the complete test sequence.

The assessment parameters used for a base position in this case are:
  Match=10;
  Mismatch=−30;
  Gap=−30.

The corresponding criterion weight SEKScore is defined as the highest alignment score $Score_{InvAlignment,max}$ reached in the checked region of the test sequence. If the value of $Score_{InvAlignment,max}$ is <100, then SEKScore is set equal to 0.

e) Sitescore

The following table lists the sequence motifs taking into account in ascertaining the SITEScore. Where a y appears on the heading "REVERSE", both the stated sequence motif and the relevant inverse complementary sequence motif was taken into account. If an n is indicated under this heading, only the stated sequence motif, but not the sequence motif inverse complementary thereto, was taken into account. For each occurrence of the sequence motifs listed in the table (or their inverse complementary if REVERSE=y) within the last 35 bases of the test sequence, the criterion weight SITEScore is increased by a value of 100 000.

| NAME | SEQUENCE | REVERSE |
| --- | --- | --- |
| KpnI | GGTACC | n |
| SacI | GAGCTC | n |
| Eukaria: (consensus) branch point | YTRAY | n |
| Eukaria: (consensus) Spice Acceptor | YYYYYYYYYN(1,10)AG | n |
| Eukaria: (consensus) Splice-Donor1 | RGGTANGT | n |
| Eukaria: poly(A)-site (1) | AATAAA | n |
| Eukaria: poly(A)-site (2) | TTTTTATA | n |
| Eukaria: poly(A)-site (3) | TATATA | n |
| Eukaria: poly(A)-site (4) | TACATA | n |
| Eukaria: poly(A)-site (5) | TAGTAGTA | n |
| Eukaria: poly(A)-site (6) | ATATATTT | n |
| Eukaria: (consensus) Splice-Donor2 | ACGTANGT | n |
| Eukaria: (Cryptic) Splice-Donor1 | RGGTNNGT | n |
| BsmBI | CGTCTC | y |
| BbsI | GAAGAC | y |
| Eukaria: (Cryptic) Splice-Donor2 | RGGTNNHT | n |
| Eukaria: (Cryptic) Splice-Donor3 | NGGTNNGT | n |
| Eukaria RNA inhib. Sequence | WWWATTTAWWW | n |

| NAME | SEQUENCE | REVERSE |
| --- | --- | --- |
| GC-Stretch | SSSSSSSSS | n |
| Chi-Sequence | GCTGGTGG | y |
| Repeats | RE (\w[9.])\1 | n |
| Prokaria: RBS-Entry (2) | AAGGAGN(3,13)ATG | y |
| Prokaria: RBS-Entry (1) | AGGAGGN(3,13)ATG | y |
| Prokaria: RBS-Entry (3) | TAASGAGGTN(3,13)DTG | y |
| Prokaria: RBS-Entry (4) | AGAGAGN(3,13)ATG | y |
| Prokaria: RBS-Entry (5) | AAGGAGGN(3,13)ATG | y |
| Prokaria: RBS-Entry (6) | AACGGAGGN(3,13)ATG | y |
| Prokaria: RBS-Entry (7) | AAGAAGGAAN(3,13)ATG | y |
| HindIII | AAGCTT | n |
| NotI | GCGGCCGC | n |
| BamHI | GGATCC | n |
| EcoRI | GAATTC | n |
| XbaI | TCTAGA | n |
| XhoI | CTCGAG | n |

The following sequences in the tables above correspond to sequences in the attached Sequence Listing Eukaria: (consensus) Spice Acceptor (SEQ ID NO: 24); Eukaria: RNA inhib. Sequence (SEQ ID NO: 25); Prokaria: RBS-Entry (2) (SEQ ID NO: 26); Prokaria: RBS-Entry (1) (SEQ ID NO: 27); Prokaria: RBS-Entry (3) (SEQ ID NO: 28); Prokaria: RBS-Entry (4) (SEQ ID NO: 29); Prokaria: RBS-Entry (5) (SEQ ID NO: 30); Prokaria: RBS-Entry (6) (SEQ ID NO: 31); Prokaria: RBS-Entry (7) (SEQ ID NO: 32).

Appropriate unique restriction cleavage sites were introduced for subcloning. The complete nucleotide sequences are indicated in the annex. The sequences modified in this way were prepared as fully synthetic genes (Geneart, Regensburg). The resulting coding DNA fragments was placed under the transcriptional control of the cytomegalo virus (CMV) early promotor/enhancer in the expression vector pcDNA3.1 (+) using the restriction cleavage sites HindIII and NotI. To prepare expression plasmids which are analogous but unaltered in their codon choice (wild-type reference constructs), the coding regions (c-DNA constructs were produced from RZPD) were cloned after PCR amplification with appropriate oligonucleotides likewise using the HindIII and NotI restriction cleavage sites in pcDNA3.1(+).

To quantify cytokine/chemokine expression, human cells were transfected with the respective expression constructs, and the amount of protein in the cells and in the cell culture supernatant was measured by using commercial ELISA test kits.

All the cell culture products were from Life Technologies (Karlsruhe). Mammalian cell lines were cultivated at 37° C. and 5% $CO_2$. The human lung carcinoma cell line H1299 was cultivated in Dulbecco's modified Eagle medium (DMEM) with L-glutamine, D-glucose (4.5 mg/ml), sodium pyruvate, 10% inactivated fetal bovine serum, penicillin (100 U/ml) and streptomycin (100 μg/ml). The cells were subcultivated in the ratio 1:10 after reaching confluence.

2.5×10⁵ cells were seeded in 6-well cell culture dishes and, after 24 h, transfected by calcium phosphate coprecipitation (Graham and Eb, 1973) with 15 µg of expression plasmids or pcDNA 3.1 vector (mock control). Cells and culture supernatants were harvested 48 h after the transfection. Insoluble constituents in the supernatants were removed by centrifugation and 10 000×g and 4° C. for 10 min. The transfected cells were washed twice with ice-cold PBS (10 mM $Na_2HPO_4$, 1.8 mM $KH_2PO_4$, 137 ml NaCl, 2.7 mM KCl), detached with 0.05% trypsin/EDTA, centrifuged at 300×g for 10 min and lysed in 100 µl of lysis buffer (50 mM Tris-HCl, pH 8.0, 150 mM NaCl, 0.1% SDS (w/v), 1% Nonidet P40 (v/v), 0.5% Na deoxycholate (w/v)) on ice for 30 min. Insoluble constituents of the cell lysate were removed by centrifugation at 10 000×g and 4° C. for 30 min. The total amount of protein in the cell lysate supernatant was determined using the Bio-Rad protein assay (Bio-Rad, Munich) in accordance with the manufacturer's instructions.

Figure 9:
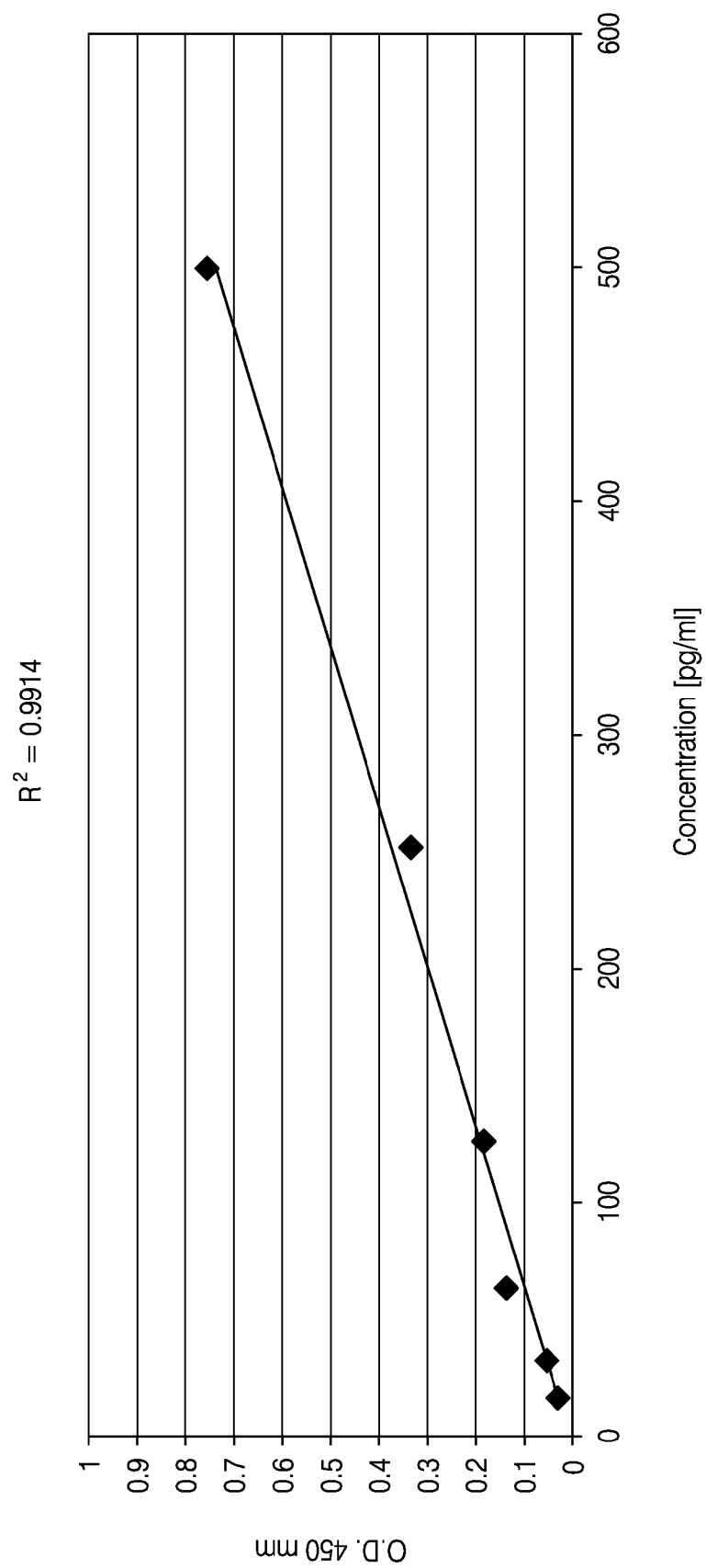
FIG. 9 shows a representative murine MIP1alpha calibration line in connection with example 3.

The specific protein concentrations in the cell lysates and cell culture supernatants were quantified by ELISA tests (BD Pharmingen for IL15 and GM-CSF; R & D Systems for MIP1alpha). Appropriate amounts of total protein of the cell lysate (0.2 to 5 µg) and dilutions of the supernatant (undiluted to 1:200) were analyzed according to the manufacturer's instructions, and the total concentration was calculated by means of a calibration plot. FIG. 9 shows a representative calibration plot for calculating the murine MIP1alpha concentration. Recombinant murine MIP1alpha was adjusted in accordance with the manufacturer's instructions by serial two-fold dilutions to increasing concentrations and employed in parallel with the samples from the cell culture experiments in the MIP1alpha specific ELISA test. The concentrations (x axis) were plotted against the measured O.D. values (450 nm, y axis), and a regression line was calculated using MS Excel (the regression coefficient $R^2$ is indicated).

Figure 12A:
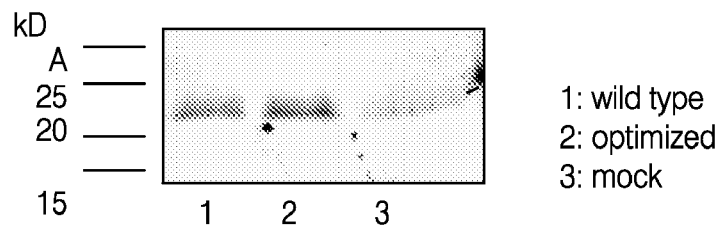
Figure 12B:
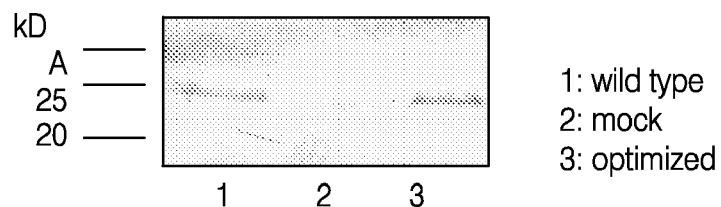
Figure 12C:
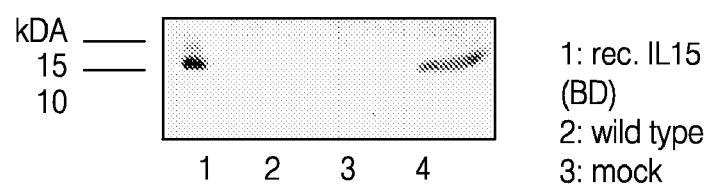

This was supplemented by carrying out a detection by Western blot analyses for suitable samples. For GM-CSF samples, total proteins were precipitated from in each case 1 ml of cell culture supernatant by Na DOC (sodium deoxycholate) and TCA (trichloroacetic acid) and resuspended in 60 µl of 1× sample buffer (Laemmli, 1970). 20 µl were employed for each of the analyses. For IL15 detection, 25 µg of total protein from cell lysates were used. The samples were heated at 95° C. for 5 min, fractionated on a 15% SDS/polyacrylamide gel (Laemmli, 1970) electrotransferred to a nitrocellulose membrane (Bio-Rad) and analyzed with appropriate monoclonal antibodies (BD Pharmingen), detected using a secondary, AP (alkaline phosphatase)-coupled antibody and demonstrated by chromogenic staining. FIG. 12A to C show the expression analysis of the synthetic reading frame and of the wild-type reading frames. H1299 cells were transfected with the stated constructs, and the protein production was detected by conventional immunoblot analyses. In this case, FIG. 12A shows the analysis of the cell culture supernatants after Na Doc/TCA precipitation of human GM-CSF transfected H1299 cells, FIG. 12B shows the analysis of the cell culture supernatants after Na Doc/TCA precipitation of murine GM-CSF transfected H1299 cells, FIG. 12C shows the analysis of the cell lysates from human IL15 transfected H1299 cells. Molecular weights (precision plus protein standard, Bio-Rad) and loading of the wild-type, synthetic and mock-transfected samples are indicated. Mock transfection corresponds to transfection with original pcDNA3.1 plasmid.

The following table summarizes the expression differences with averages of all ELISA-analyzed experiments. The data correspond to the percentage difference in the total amount of protein (total amount of protein in cell lysate and supernatant) related to the corresponding wild-type construct (wt corresponds to 100%).

Comparison of the Total Amounts of Protein after Transfection of Wild-Type vs. Synthetic Expression Constructs

| Construct  | Organism | MW*  | StdDev** | n= |
|------------|----------|------|----------|----|
| GM-CSF     | human    | 173% | 53%      | 4  |
| IL15       | human    | 181% | 37%      | 3  |
| GM-CSF     | mouse    | 127% | 12%      | 2  |
| MIP11alpha | mouse    | 146% | 48%      | 2  |

Figure 10:
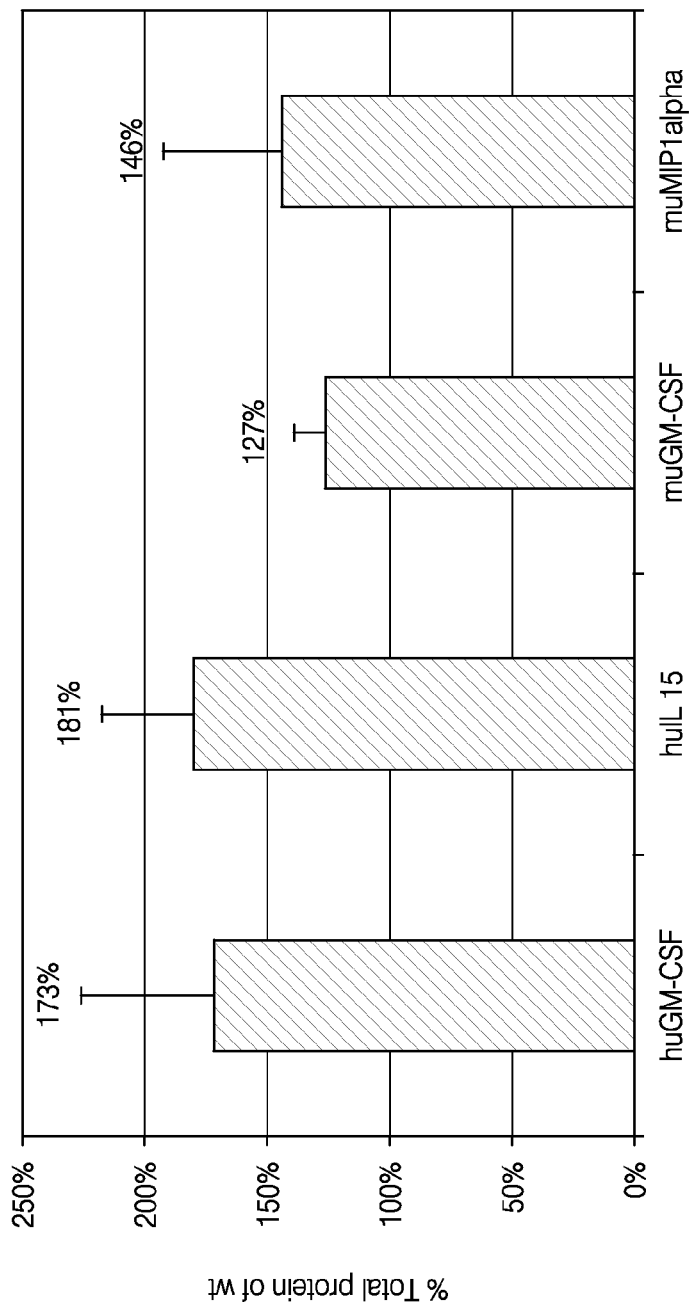
FIG. 10 illustrates the percentage increase in the total amount of protein after transfection of synthetic expression constructs compared with wild-type expression constructs in connection with example 3.

*percentage average of the amount of protein from n experiments (in duplicate) related to the total amount of protein for the corresponding wild-type construct
**standard deviation FIG. 10 shows in the form of a bar diagram the relative amount of protein in relation to the respective wild-type construct (corresponds to 100%) and illustrates the percentage increase in the total amount of protein after transvection of synthetic expression constructs compared with wild-type expression constructs. H1299 cells were transfected with 15 µg of the stated cytokine/chemokine constructs. The respective protein production was quantified by conventional ELISA tests in the cell culture supernatant and in the cell lysate by means of appropriate standard plots (see FIG. 9). The ratio of the total amount of protein of synthetic to wild-type protein was calculated in each experiment (consisting of two independent mixtures) and indicated as percent of the total wild-type protein. The bars represent the average of four experiments for human GM-CSF, of three experiments for human IL15 and of two experiments for murine MIP1alpha and GM-CSF, in each case in independent duplicates. The error bars correspond to the standard deviation.

Figure 11:
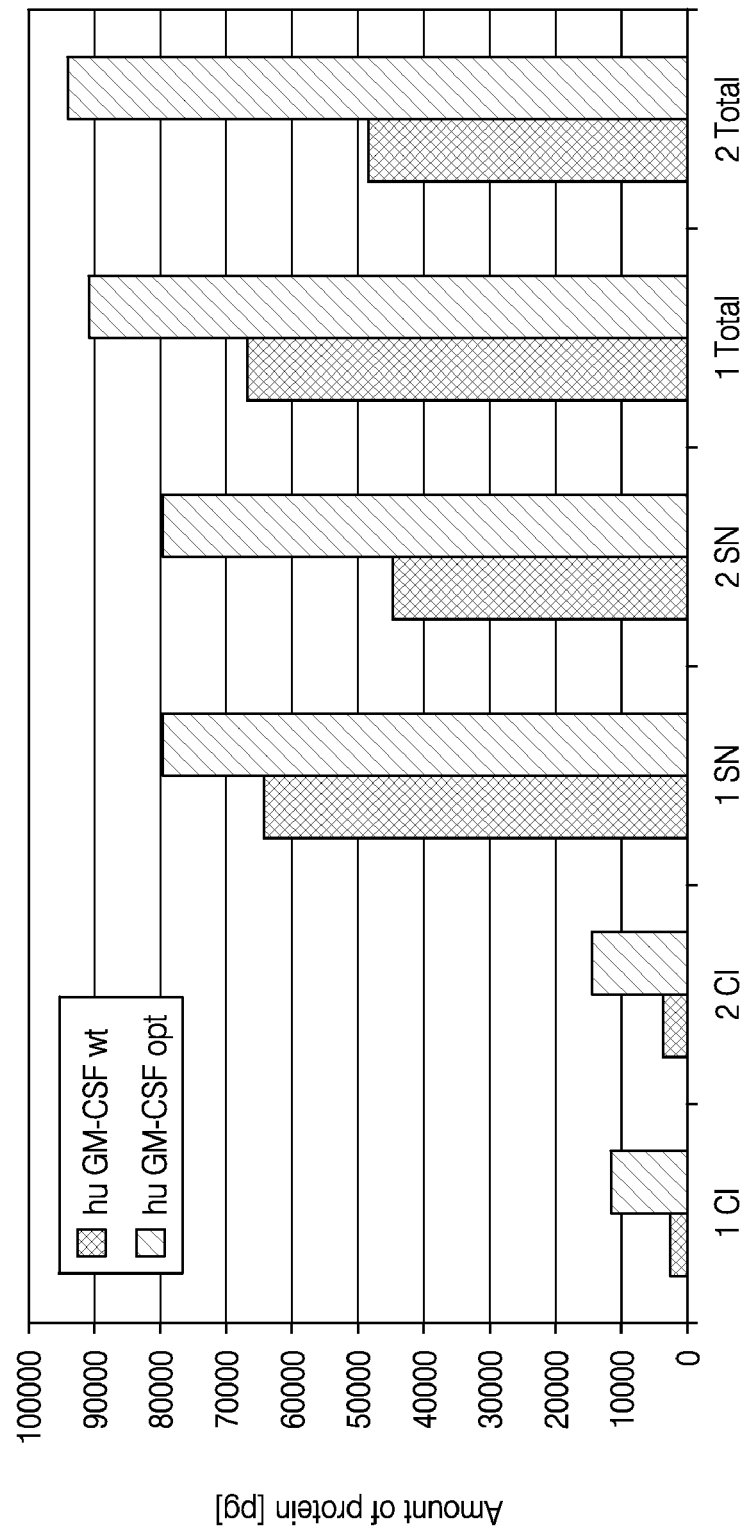
FIG. 11 shows a representative ELISA analysis of the cell lysates and supernatants of transfected H1299 cells in connection with example 3 and FIG. 12A to 12C shows the expression analysis of the synthetic reading frames and of the wild-type reading frames in connection with example 3.

FIG. 11 depicts a representative ELISA analysis of the cell lysates and supernatants of transfected H1299 cells for human GM-CSF. H1299 cells were transfected with 15 µg each of wild-type and optimized human GM-CSF constructs. The respective protein concentration was quantified by conventional ELISA tests in the cell culture supernatant and in the cell lysate by means of appropriate standard plots. The bars represent the value of the total amount of protein in the cell lysate (CL), in the cell culture supernatant (SN) and the total of these values (total) for in each case 2 independent mixtures (1 and 2).

This analysis shows that the increase in expression after optimization (hu GM-CSF opt) is consistently detectable in the cell lysate and supernatant. It also illustrates by way of example that secretion of the cytokines is unaffected by the optimization by this method. A distinct and reproducible increase in protein expression was detectable for all optimized constructs, with the synthesis efficiencies of the optimized genes being improved by comparison with the wild-type genes in each individual experiment.

Expression was additionally checked in Western blot analyses (FIG. 12A to C). Human and murine GM-CSF were detectable in the cell culture supernatant (after Na DOC/TCA precipitation) (FIGS. 12A and B), while human IL15 was detectable in the cell lysates (FIG. 12C). The proteins were analyzed, compared with commercially available recombinant proteins (BD) and the molecular weight was correspondingly confirmed. It was not possible in these transient transfection experiments to detect murine MIP1alpha by immunoblot staining. Comparison of the wild-type with the synthetic proteins in these representative immunoblots confirms the data of the ELISA analyses of an improved protein synthesis through multiparameter optimization of these genes.

The features disclosed in the claims, the drawings and the description may be essential both singly and in any combination for implementation of the invention in its various embodiments.

Annex: SEQ-IDs and alignments of the DNA sequences used

The SEQ-ID references used herein correspond to the similarly-numbered sequences in the attached Sequence Listing, e.g., "SEQ-ID1" corresponds to SEQ ID NO: 1, "SEQ-ID2" corresponds to SEQ ID NO: 2, etc.

SEQ-ID of the indicated constructs:

```
SEQ-ID1 (human GM-CSF wild type):
   1 atgtggctgc agagcctgct gctcttgggc actgtggcct gcagcatctc tgcacccgcc 61 cgctcgccca gccccagcac gcagccctgg gagcatgtga atgccatcca ggaggccgg 121 cgtctcctga acctgagtag agacactgct gctgagatga cgaaacagt agaagtcatc 181 tcagaaatgt ttgacctcca ggagccgacc tgcctacaga cccgcctgga gctgtacaag 241 cagggcctgc ggggcagcct caccaagctc aagggcccct tgaccatgat ggccagccac 301 tacaagcagc actgccctcc aacccggaa acttcctgtg caacccagat tatcacctt 361 gaaagtttca aagagaacct gaaggacttt ctgcttgtca tcccctttga ctgctgggag 421 ccagtccagg agtag SEQ-ID2 (human GM-CSF optimized):
   1 atgtggctgc agagcctgct gctgctggga acagtggcct gtagcatctc tgcccctgcc 61 agaagcccta gcctagcac acagccttgg gagcacgtga atgccatcca ggaggccagg 121 agactgctga acctgagcag agatacagcc gccgagatga cgagaccgt ggaggtgatc 181 agcgagatgt tcgacctgca ggagcctaca tgcctgcaga cccggctgga gctgtataag 241 cagggcctga gaggctctct gaccaagctg aagggccccc tgacaatgat ggccagccac 301 tacaagcagc actgccctcc taccctgag acaagctgcg ccacccagat catcaccttc 361 gagagcttca aggagaacct gaaggacttc ctgctggtga tccccttga ttgctgggag 421 cccgtgcagg agtag SEQ-ID3 (human IL15 wild type):
   1 atgagaattt cgaaaccaca tttgagaagt atttccatcc agtgctactt gtgtttactt 61 ctaaacagtc attttctaac tgaagctggc attcatgtct tcattttggg ctgtttcagt 121 gcagggcttc ctaaaacaga gccaactgg gtgaatgtaa taagtgattt gaaaaaaatt 181 gaagatctta ttcaatctat gcatattgat gctacttat atacggaaag tgatgttcac 241 cccagttgca aagtaacagc aatgacgtgc tttctcttgg agttacaagt tatttcactt 301 gagtccggag atgcaagtat tcatgataca gtagaaaatc tgatcatcct agcaaacaac 361 agtttgtctt ctaatgggaa tgtaacagaa tctggatgca aagaatgtga ggaactggag 421 gaaaaaaata ttaaagaatt tttgcagagt tttgtacata ttgtccaaat gttcatcaac 481 acttcttag SEQ-ID4 (human IL15 optimized):
   1 acgcggatca gcaagcccca cctgaggagc atcagcatcc agtgctacct gtgcctgctg 61 ctgaacagcc acttcctgac agaggccggc atccacgtgt ttatcctggg ctgcttctct 121 gccggcctgc ctaagacaga ggccaactgg gtgaacgtga tcagcgacct gaagaagatc 181 gaggacctga tccagagcat gcacatcgac gccaccctgt acacagagag cgacgtgcac 241 cctagctgta aggtgaccgc catgaagtgc ttcctgctgg agctgcaggt gatcagcctg 301 gagagcggcg atgccagcat ccacgacacc gtggagaacc tgatcatcct ggccaacaac 361 agcctgagca gcaacggcaa tgtgaccgag agcggctgca aggagtgtga ggagctggag 421 gagaagaaca tcaaggagtt cctgcagagc ttcgtgcaca tcgtgcagat gttcatcaac 481 accagctag
```

-continued

SEQ-ID5 (murine GM-CSF wild type):
```
  1 atgtggctgc agaatttact tttcctgggc attgtggtct acagcctctc agcacccacc
 61 cgctcaccca tcactgtcac ccggccttgg aagcatgtag aggccatcaa agaagccctg
121 aacctcctgg atgacatgcc tgtcacattg aatgaagagg tagaagtcgt ctctaacgag
181 ttctccttca agaagctaac atgtgtgcag acccgcctga agatattaga gcagggtcta
241 cggggcaatt tcaccaaact caagggcgcc ttgaacatga cagccagcta ctaccagaca
301 tactgccccc caactccgga aacggactgt gaaacacaag ttaccaccta tgcggatttc
361 atagacagcc ttaaaacctt tctgactgat atcccctttg aatgcaaaaa accaggccaa
421 aaatag
```

SEQ-ID6 (murine GM-CSF optimized):
```
  1 atgtggctgc agaacctgct gttcctgggc atcgtggtgt acagcctgag cgcccccacc
 61 aggagcccca tcaccgtgac caggccctgg aagcacgtgg aggccatcaa ggaggccctg
121 aacctgctgg acgacatgcc cgtgaccctg aacgaggagg tggaggtggt gagcaacgag
181 ttcagcttca agaagctgac ctgcgtgcag accaggctga agatcttcga gcagggcctg
241 aggggcaact tcaccaagct gaagggcgcc ctgaacatga ccgccagcta ctaccagacc
301 tactgccccc ccacccccga ccgactgc gagacccagg tgaccaccta cgccgacttc
361 atcgacagcc tgaagacctt cctgaccgac atccccttcg agtgcaagaa gcccggccag
421 aagtag
```

SEQ-ID7 (murine MIPIapha wild type):
```
  1 atgaaggtct ccaccactgc ccttgctgtt cttctctgta ccatgacact ctgcaaccaa
 61 gtcttctcag cgccatatgg agctgacacc ccgactgcct gctgcttctc ctacagccgg
121 aagattccac gccaattcat cgttgactat tttgaaacca gcagcctttg ctcccagcca
181 ggtgtcattt tcctgactaa gagaaaccgg cagatctgcg ctgactccaa agagacctgg
241 gtccaagaat acatcactga cctggaactg aatgcctag
```

SEQ-ID8 (murine MIPIapha optimized):
```
  1 atgaaggtga gcaccacagc tctggctgtg ctgctgtgca ccatgaccct gtgcaaccag
 61 gtgttcagcg ctccttacgg cgccgatacc cctacagcct gctgcttcag ctacagcagg
121 aagatcccca ggcagttcat cgtggactac ttcgagacca gcagcctgtg ttctcagccc
181 ggcgtgatct tcctgaccaa gcggaacaga cagatctgcg ccgacagcaa ggagacatgg
241 gtgcaggagt acatcaccga cctggagctg aacgcctag
```

Alignments of the DNA Sequences used

1. Human GM-CSF:
Upper line: SEQ-ID1 (human GM-CSF wild type), from 1 to 435
Lower line: SEQ-ID2 (human GM-CSF optimized), from 1 to 435
Wild type: optimized identity=83.45% (363/435) gap=0.00% (0/435)

```
  1 ATGTGGCTGCAGAGCCTGCTGCTCTTGGGCACTGTGGCCTGCAGCATCTCTGCACCCGCC
    ||||||||||||||||||||||||| |||| || |||||||| |||||||||||| || ||
  1 ATGTGGCTGCAGAGCCTGCTGCTGCTGGGAACAGTGGCCTGTAGCATCTCTGCCCCTGCC

61 CGCTCGCCCAGCCCCAGCACGCAGCCCTGGGAGCATGTGAATGCCATCCAGGAGGCCCGG
    |    ||  ||||||  |||||   ||||||||  |||||||||||||||||||||  ||
 61 AGAAGCCCTAGCCCCTAGCACACAGCCTTGGGAGCACGTGAATGCCATCCAGGAGGCCAGG
```

-continued

```
121 CGTCTCCTGAACCTGAGTAGAGACACTGCTGCTGAGATGAATGAAACAGTAGAAGTCATC
    | ||| |||||||||||| |||||  || || ||||||||  ||||  ||| || ||||
121 AGACTGCTGAACCTGAGCAGAGATACAGCCGCCGAGATGAACGAGACCGTGGAGGTGATC

181 TCAGAAATGTTTGACCTCCAGGAGCCGACCTGCCTACAGACCCGCCTGGAGCTGTACAAG
    || ||||| |||| ||||||||||||| || || ||||| ||||||||||||||| |||
181 AGCGAGATGTTCGACCTGCAGGAGCCTACATGCCTGCAGACCCGGCTGGAGCTGTATAAG

241 CAGGGCCTGCGGGGCAGCCTCACCAAGCTCAAGGGCCCCTTGACCATGATGGCCAGCCAC
    |||||||||  |||  ||||   ||||||||||||||  ||||||| ||||||||||||||
241 CAGGGCCTGAGAGGCTCTCTGACCAAGCTGAAGGGCCCCCTGACAATGATGGCCAGCCAC

301 TACAAGCAGCACTGCCCTCCAACCCCGGAAACTTCCTGTGCAACCCAGATTATCACCTTT
    |||||||||||||||||| || ||| ||    ||| || ||| ||||||||| ||||||
301 TACAAGCAGCACTGCCCTCCTACCCCTGAGACAAGCTGCGCCACCCAGATCATCACCTTC

361 GAAAGTTTCAAAGAGAACCTGAAGGACTTTCTGCTTGTCATCCCCTTTGACTGCTGGGAG
    || || ||||  |||||||||||||||| ||||||| || |||||| || ||||||||||
361 GAGAGCTTCAAGGAGAACCTGAAGGACTTCCTGCTGGTGATCCCCTTCGATTGCTGGGAG

421 CCAGTCCAGGAGTAG
    || ||  ||||||||
421 CCCGTGCAGGAGTAG
```

2. Human IL15:
Upper line: SEQ-ID3 (human IL15 wild type), from 1 to 489
Lower line: SEQ-ID4 (human IL15 optimized), from 1 to 489
Wild type: optimized identity=70.55% (345/489) gap=0.00% (0/489)

3. Murine GM-CSF:
Upper line: SEQ-ID5 (murine GM-CSF wild type), from 1 to 426
Lower line: SEQ-ID6 (murine GM-CSF optimized), from 1 to 426
Wild type: optimized identity=80.75% (344/426) gap=0.00% (0/426)

```
  1 ATGAGAATTTCGAAACCACATTTGAGAAGTATTTCCATCCAGTGCTACTTGTGTTTACTT
    |||  | ||    || ||  |||| || ||  || ||||||||||||||| |||  |||
  1 ATGCGGATCAGCAAGCCCCACCTGAGGAGCATCAGCATCCAGTGCTACCTGTGCCTGCTG

61 CTAAACAGTCATTTTCTAACTGAAGCTGGCATTCATGTCTTCATTTTGGGCTGTTTCAGT
    || ||||| ||||| ||||| ||| |||||||| |||||| ||| |||||||||  |||
 61 CTGAACAGCCACTTCCTGACAGAGGCCGGCATCCACGTGTTTATCCTGGGCTGCTTCTCT

121 GCAGGGCTTCCTAAAACAGAAGCCAACTGGGTGAATGTAATAAGTGATTTGAAAAAAATT
    || || || || ||| |||| |||||||||||| ||| ||| || || || |||||||
121 GCCGGCCTGCCTAAGACAGAGGCCAACTGGGTGAACGTGATCAGCGACCTGAAGAAGATC

181 GAAGATCTTATTCAATCTATGCATATTGATGCTACTTTATATACGGAAAGTGATGTTCAC
    || || || ||  |||| ||||| || || ||| ||  ||| ||| | || |||| |||
181 GAGGACCTGATCCAGAGCATGCACATCGACGCCACCCTGTACACAGAGAGCGACGTGCAG

241 CCCAGTTGCAAAGTAACAGCAATGAAGTGCTTTCTCTTGGAGTTACAAGTTATTTCACTT
    || || || ||||| || ||||| ||||||| || |||||| ||||||| |||| ||
241 CCTAGCTGTAAGGTGACCGCCATGAAGTGCTTCCTGCTGGAGCTGCAGGTGATCAGCCTG

301 GAGTCCGGAGATGCAAGTATTCATGATACAGTAGAAAATCTGATCATCCTAGCAAACAAC
    ||| || || ||||| |||  ||||| |  | ||| ||| ||||||||  || |||||
301 GAGAGCGGCGATGCCAGCATCCACGACACCGTGGAGAACCTGATCATCCTGGCCAACAAC

361 AGTTTGTCTTCTAATGGGAATGTAACAGAATCTGGATGCAAAGAATGTGAGGAACTGGAG
    || ||   |  ||| |||  |||  || || ||  |||||  ||||||||||| |||||
361 AGCCTGAGCAGCAACGGCAATGTGACCGAGAGCGGCTGCAAGGAGTGTGAGGAGCTGGAG

421 GAAAAAATATTAAAGAATTTTTGCAGAGTTTTGTACATATTGTCCAAATGTTCATCAAC
    || ||   || ||||||||| ||||||| || ||||| |||| |  |||||||||||||
421 GAGAAGAACATCAAGGAGTTCCTGCAGAGCTTCGTGCACATCGTGCAGATGTTCATCAAC

481 ACTTCTTAG
    ||   |||
481 ACCAGCTAG
```

```
  1 ATGTGGCTGCAGAATTTACTTTTCCTGGGCATTGTGGTCTACAGCCTCTCAGCACCCACC
    ||||||||||||||  |  ||  ||||||||||| |||||  ||||||||     ||  |||||||
  1 ATGTGGCTGCAGAACCTGCTGTTCCTGGGCATCGTGGTGTACAGCCTGAGCGCCCCCACC

61 CGCTCACCCATCACTGTCACCCGGCCTTGGAAGCATGTAGAGGCCATCAAAGAAGCCCTG
    |         ||||||||| || ||| ||||  ||||||||| ||  ||||||||||| || |||||||
 61 AGGAGCCCCATCACCGTGACCAGGCCCTGGAAGCACGTGGAGGCCATCAAGGAGGCCCTG

121 AACCTCCTGGATGACATGCCTGTCACATTGAATGAAGAGGTAGAAGTCGTCTCTAACGAG
    |||||  |||||  ||||||||| ||  ||   ||||  ||  ||||| ||  ||  ||      ||||||
121 AACCTGCTGGACGACATGCCCGTGACCCTGAACGAGGAGGTGGAGGTGGTGAGCAACGAG

181 TTCTCCTTCAAGAAGCTAACATGTGTGCAGACCCGCCTGAAGATATTCGAGCAGGGTCTA
    |||  |||||||||||||||||  ||  |||||||||  |  |||||||||||  |||||||||||||||||  ||
181 TTCAGCTTCAAGAAGCTGACCTGCGTGCAGACCAGGCTGAAGATCTTCGAGCAGGGCCTG

241 CGGGGCAATTTCACCAAACTCAAGGGCGCCTTGAACATGACAGCCAGCTACTACCAGACA
    |||||||  ||||||||  ||  |||||||||||  ||||||||||||  |||||||||||||||||||
241 AGGGGCAACTTCACCAAGCTGAAGGGCGCCCTGAACATGACCGCCAGCTACTACCAGACC

301 TACTGCCCCCCAACTCCGGAAACGGACTGTGAAACACAAGTTACCACCTATGCGGATTTC
    ||||||||||||  ||  || ||  ||  |||||  ||  ||  ||  ||||||||| ||  || |||
301 TACTGCCCCCCACCCCCGAGACCGACTGCGAGACCCAGGTGACCACCTACGCCGACTTC

361 ATAGACAGCCTTAAAACCTTTCTGACTGATATCCCCTTTGAATGCAAAAAACCAGGCCAA
    || ||||||||| || ||||| ||||| || || |||||||| |||||| || || ||||||
361 ATCGACAGCCTGAAGACCTTCCTGACCGACATCCCCTTCGAGTGCAAGAAGCCCGGCCAG

421 AAATAG
    || |||
421 AAGTAG
```

4. Murine MIP1alpha:

Upper line: SEQ-ID7 (murine MIP1alpha wild type), from 1 to 279

Lower line: SEQ-ID8 (murine MIP1alpha optimized), from 1 to 279

Wild type: optimized identity=78.49% (219/279) gap=0.00% (0/279)

```
  1 ATGAAGGTCTCCACCACTGCCCTTGCTGTTCTTCTCTGTACCATGACACTCTGCAACCAA
    ||||||||   ||||||  || || ||||| || || ||  ||||||||| ||  ||||||||||
  1 ATGAAGGTGAGCACCACAGCTCTGGCTGTGCTGCTGTGCACCATGACCCTGTGCAACCAG

61 GTCTTCTCAGCGCCATATGGAGCTGACACCCCGACTGCCTGCTGCTTCTCCTACAGCCGG
    ||  |||  ||||| ||   ||  ||||  ||||  ||||||| ||||||||||  ||||||||||||
 61 GTGTTCAGCGCTCCTTACGGCGCCGATACCCCTACAGCCTGCTGCTTCAGCTACAGCAGG

121 AAGATTCCACGCCAATTCATCGTTGACTATTTTGAAACCAGCAGCCTTTGCTCCCAGCCA
    ||||| ||  ||  |||||||||| ||||| || ||  |||||||||||||| || || ||||||
121 AAGATCCCCAGGCAGTTCATCGTGGACTACTTCGAGACCAGCAGCCTGTGTTCTCAGCCC

181 GGTGTCATTTTCCTGACTAAGAGAAACCGGCAGATCTGCGCTGACTCCAAAGAGACCTGG
    ||  ||  || |||||||||||  ||| ||| | ||||||||||||| ||||  |||  |||  ||
181 GGCGTGATCTTCCTGACCAAGCGGAACAGACAGATCTGCGCCGACAGCAAGGAGACATGG

241 GTCCAAGAATACATCACTGACCTGGAACTGAATGCCTAG
    ||  ||  || ||||||||||  ||||||||||  |||||  ||||||
241 GTGCAGGAGTACATCACCGACCTGGAGCTGAACGCCTAG
```

The invention claimed is:

1. A computerized method for optimizing a nucleotide sequence for the expression of a protein on the basis of the amino acid sequence of the protein, which comprises the following steps:
generating, using a suitably programmed computer, a first test sequence of n codons which correspond to n consecutive amino acids in the protein sequence, where n is a natural number and is less than N, the number of amino acids in the protein sequence,
specifying, using the suitably programmed computer, m optimization positions in the test sequence which correspond to the position of m codons at which the occupation by a codon, relative to the test sequence, is to be optimized, where $m \leq n$ and $m<N$,
generating, using the suitably programmed computer, one or more further test sequences from the first test sequence by replacing at one or more of the m optimization positions a codon of the first test sequence by another codon which expresses the same amino acid,
assessing, using the suitably programmed computer, each of the test sequences with a quality function and ascertaining the test sequence which is optimal in relation to the quality function,
specifying, using the suitably programmed computer, p codons of the optimal test sequence which are located at one of the m optimization positions, as result codons which form the codons of the optimized nucleotide sequence at the positions which corresponds to the position of said p codons in the test sequence, where p is a natural number and $p \leq m$,
iterating the preceding steps, where in each iteration step the test sequence comprises the appropriate result codon at the positions which correspond to positions of specified result codons in the optimized nucleotide sequence, and the optimization positions are different from positions of result codons.

2. The method as claimed in claim 1, wherein in one or more iteration steps the m optimization positions of the test sequences directly follow one or more result codons which have been specified as part of the optimized nucleotide sequence.

3. The method as claimed in claim 1, wherein in one or more iteration steps the p codons which are specified as result codons of the optimized nucleotide sequence are p consecutive codons.

4. The method as claimed in claim 1, wherein in one iteration step test sequences with all possible codon occupations for the m optimization positions are generated from the first test sequence, and the optimal test sequence is ascertained from these test sequences.

5. The method as claimed in claim 1, wherein:
each test sequence is assessed with a quality function,
an extreme value is ascertained within the values of the quality function for all partial sequences generated in an iteration step,
p codons of the test sequence are specified which corresponds to the extreme value of the weight function as result codons at the appropriate positions, where p is a natural number and $p \geq m$.

6. The method as claimed in claim 5, wherein the quality function takes account of one or more of the following criteria:
codon usage for a predefined organism, GC content, repetitive sequences, secondary structures, inverse complementary sequence repeats and sequence motifs.

7. The method as claimed in claim 6, wherein the quality function is a function of various single terms which in each case assess one criterion from the following list of criteria:
codon usage for a predefined organism, GC content, sequence motifs, repetitive sequences, secondary structures, inverse complementary sequence repeats.

8. The method as claimed in claim 1, wherein the quality function takes account of one or more of the following criteria:
exclusion of inverse complementary sequence identities of more than 20 nucleotides to the transcriptome of a predefined organism,
exclusion of homology regions of more than 100 base pairs to a predefined DNA sequence,
exclusion of homology regions with more than 90% similarity of the nucleotide sequence to a predefined DNA sequence.

9. The method as claimed in claim 1, further comprising synthesizing the optimized nucleotide sequence.

10. The method as claimed in claim 9, wherein the step of synthesizing the optimized nucleotide sequence takes place in a device for automatic synthesis of nucleotide sequences which is controlled by the computer which optimizes the nucleotide sequence.

11. A device for optimizing a nucleotide sequence for the expression of a protein on the basis of the amino acid sequence of the protein, which has a computer unit comprising algorithms, including:
an algorithm for generation of a first test sequence of n codons which correspond to n consecutive amino acids in the protein sequence, where n is a natural number and is less than N, the number of amino acids in the protein sequence,
an algorithm for specification of m optimization positions in the test sequence which correspond to the position of m codons at which the occupation by a codon, relative to the test sequence, is to be optimized, where in m≦n and m<N, an algorithm for generation of one or more further test sequences from the first test sequence by replacing at one or more of the m optimization positions a codon of the first test sequence by another codon which expresses the same amino acid, an algorithm for assessment of each of the test sequences with a quality function and for ascertaining the test sequence which is optimal in relation to the quality function, an algorithm for specification of p codons of the optimal test sequence which are located at one of the m optimization positions, as result codons which form the codons of the optimized nucleotide sequence at the positions which correspond to the positions of said p codons in the test sequence, where p is a natural number and p≦m, an algorithm for iteration of the steps of generation of a plurality of test functions, of assessment of the test sequences and of specification of result codons, wherein each iteration step the test sequence comprises the appropriate result codon at the positions which correspond to positions of specified result codons in the optimized nucleotide sequence, and the optimization positions are different from positions of result codons.

12. The device as claimed in claim 11, further comprising an algorithm for carrying out the steps of a method as claimed in claim 1.

13. The device as claimed in claim 11, further comprising a device for automatic synthesis of nucleotide sequences which is controlled by the computer in such a way that it synthesizes the optimized nucleotide sequence.

14. A computer program product comprising instructions encoded on a non-transitory computer readable medium, wherein the instructions are executable by a computer to cause the computer to carry out a method as claimed in claim 1.

15. The computer program product as claimed in claim 14, where the instructions can, when executed by a computer, cause a device for the automatic synthesis of nucleotide sequences to prepare the optimized nucleotide sequence.

16. A computerized method for optimizing a nucleotide sequence for the expression of a protein on the basis of the amino acid sequence of the protein, which comprises the following:

generating, using a suitably programmed computer, a first test sequence of n codons which correspond to n consecutive amino acids in the protein sequence, where n is a natural number and is less than N, the number of amino acids in the protein sequence, specifying, using the suitably programmed computer, m optimization positions in the test sequence which correspond to the position of m codons at which the occupation by a codon, relative to the test sequence, is to be optimized, where m≦n and m<N, generating, using the suitably programmed computer, one or more further test sequences from the first test sequence by replacing at one or more of the m optimization positions a codon of the first test sequence by another codon which expresses the same amino acid, assessing, using the suitably programmed computer, each of the test sequences with a quality function and ascertaining the test sequence which is optimal in relation to the quality function, specifying, using the suitably programmed computer, p codons of the optimal test sequence which are located at one of the m optimization positions, as result codons which form the codons of the optimized nucleotide sequence at the positions which corresponds to the position of said p codons in the test sequence, where p is a natural number and p≦m, iterating the preceding steps, where in each iteration step the test sequence comprises the appropriate result codon at the positions which correspond to positions of specified result codons in the optimized nucleotide sequence, and the optimization positions are different from positions of result codons, and wherein after said result codons are specified in any iteration step, the result codons are not changed in subsequent iterations.

17. The method according to claim 16, wherein at least some of the m optimization positions are connected and form a variation window on which codon occupation is to be varied.

18. The method according to claim 17, wherein the variation window in one iteration step overlaps with the variation window of a preceding iteration step.

19. The method according to claim 17, wherein the variation window has a size of m=3 to m=20.

20. The method according to claim 19, wherein the variation window has a size of m=5 to m=10.

21. A computerized method for optimizing a nucleotide sequence for the expression of a protein on the basis of the amino acid sequence of the protein, which comprises the following steps performed on one or more suitably programmed computers:

generating a first test sequence of n codons which correspond to n consecutive amino acids in the protein sequence, where n is a natural number and is less than N, the number of amino acids in the protein sequence, specifying m optimization positions in the test sequence which correspond to the position of m codons at which the occupation by a codon, relative to the test sequence, is to be optimized, where m≦n and m<N, generating one or more further test sequences from the first test sequence by replacing at one or more of the m optimization positions a codon of the first test sequence by another codon which expresses the same amino acid, assessing each of the test sequences with a quality function and ascertaining the test sequence which is optimal in relation to the quality function, specifying p codons of the optimal test sequence which are located at one of the m optimization positions, as result codons which form the codons of the optimized nucleotide sequence at the positions which corresponds to the position of said p codons in the test sequence, where p is a natural number and p≦m, iterating the preceding steps, where in each iteration step the test sequence comprises the appropriate result codon at the positions which correspond to positions of specified result codons in the optimized nucleotide sequence, and the optimization positions are different from positions of result codons.

22. A computerized method for optimizing a nucleotide sequence for the expression of a protein on the basis of the amino acid sequence of the protein, which comprises the following performed on one or more suitably programmed computers:

generating a first test sequence of n codons which correspond to n consecutive amino acids in the protein sequence, where n is a natural number and is less than N, the number of amino acids in the protein sequence, specifying m optimization positions in the test sequence which correspond to the position of m codons at which the occupation by a codon, relative to the test sequence, is to be optimized, where $m \leqq n$ and $m<N$, generating one or more further test sequences from the first test sequence by replacing at one or more of the m optimization positions a codon of the first test sequence by another codon which expresses the same amino acid, assessing each of the test sequences with a quality function and ascertaining the test sequence which is optimal in relation to the quality function, specifying p codons of the optimal test sequence which are located at one of the m optimization positions, as result codons which form the codons of the optimized nucleotide sequence at the positions which corresponds to the position of said p codons in the test sequence, where p is a natural number and $p \leqq m$, iterating the preceding steps, where in each iteration step the test sequence comprises the appropriate result codon at the positions which correspond to positions of specified result codons in the optimized nucleotide sequence, and the optimization positions are different from positions of result codons, and wherein after said result codons are specified in any iteration step, the result codons are not changed in subsequent iterations.

* * * * *